US009487672B2

(12) United States Patent
Cavallin et al.

(10) Patent No.: US 9,487,672 B2
(45) Date of Patent: *Nov. 8, 2016

(54) POLYURETHANE COATING COMPOSITION

(71) Applicant: Valspar Sourcing, Inc., Minneapolis, MN (US)

(72) Inventors: Carl Cavallin, Albertville, MN (US); T Howard Killilea, North Oaks, MN (US); Larry Brandenburger, Lino Lakes, MN (US); Dan Hartinger, Hudson, WI (US)

(73) Assignee: Valspar Sourcing, Inc., Minneapolis, MN (US)

( * ) Notice: Subject to any disclaimer, the term of this patent is extended or adjusted under 35 U.S.C. 154(b) by 106 days.

This patent is subject to a terminal disclaimer.

(21) Appl. No.: 14/464,217

(22) Filed: Aug. 20, 2014

(65) Prior Publication Data

US 2015/0037592 A1 Feb. 5, 2015

Related U.S. Application Data

(63) Continuation of application No. 13/496,758, filed as application No. PCT/US2010/049356 on Sep. 17, 2010, now Pat. No. 8,840,966, and a continuation-in-part of application No. PCT/US2010/042254, filed on Jul. 16, 2010.

(60) Provisional application No. 61/300,647, filed on Feb. 2, 2010, provisional application No. 61/243,888, filed on Sep. 18, 2009.

(51) Int. Cl.
| | |
|---|---|
| C09D 175/14 | (2006.01) |
| B05D 7/14 | (2006.01) |
| C08F 283/00 | (2006.01) |
| C08G 18/08 | (2006.01) |
| C08G 18/12 | (2006.01) |
| C08G 18/48 | (2006.01) |
| C08G 18/69 | (2006.01) |
| C08G 18/75 | (2006.01) |
| C08L 75/04 | (2006.01) |
| C09D 151/08 | (2006.01) |
| C08K 5/06 | (2006.01) |
| C08G 64/04 | (2006.01) |
| C08G 63/676 | (2006.01) |
| B32B 1/08 | (2006.01) |
| C07C 37/20 | (2006.01) |
| C07C 37/68 | (2006.01) |
| C07C 39/16 | (2006.01) |
| B05D 3/02 | (2006.01) |
| B32B 15/08 | (2006.01) |
| C08L 67/06 | (2006.01) |
| C09D 167/06 | (2006.01) |

(52) U.S. Cl.
CPC ........... *C09D 175/14* (2013.01); *B05D 3/0254* (2013.01); *B05D 7/14* (2013.01); *C08F 283/008* (2013.01); *C08G 18/0823* (2013.01); *C08G 18/12* (2013.01); *C08G 18/4891* (2013.01); *C08G 18/698* (2013.01); *C08G 18/755* (2013.01); *C08L 75/04* (2013.01); *C09D 151/08* (2013.01); *B05D 3/02* (2013.01); *B32B 1/08* (2013.01); *B32B 15/08* (2013.01); *C07C 37/20* (2013.01); *C07C 37/68* (2013.01); *C07C 39/16* (2013.01); *C08G 63/676* (2013.01); *C08G 64/04* (2013.01); *C08K 5/06* (2013.01); *C08L 67/06* (2013.01); *C09D 167/06* (2013.01); *Y10T 428/1352* (2015.01); *Y10T 428/1355* (2015.01); *Y10T 428/264* (2015.01); *Y10T 428/31551* (2015.04); *Y10T 428/31605* (2015.04); *Y10T 428/31692* (2015.04)

(58) Field of Classification Search
CPC .. C08G 18/12; C08G 18/698; C08G 18/755; C08G 18/676; C08G 18/0823; C08G 18/3271; C08G 18/4891; C08G 64/04; C08F 220/18; C08F 220/32; C08F 283/008; C08L 67/06; C08L 75/04; C08L 75/14; C08L 2666/02; C08L 2666/04; C08K 5/06; C07C 37/20; C07C 37/68; C07C 39/16; B32B 1/08; B32B 15/08; Y10T 428/264; Y10T 428/1352; Y10T 428/1355; Y10T 428/31551; Y10T 428/31605; Y10T 428/31692
USPC ............... 428/423.1; 524/590; 427/388.2
See application file for complete search history.

(56) References Cited

U.S. PATENT DOCUMENTS

| | | | |
|---|---|---|---|
| 2,633,458 | A | 3/1953 | Shokal |
| 3,242,123 | A | 3/1966 | Mayfield et al. |

(Continued)

FOREIGN PATENT DOCUMENTS

| | | |
|---|---|---|
| CA | 2073159 A1 | 1/1993 |
| EP | 0522400 A2 | 1/1993 |

(Continued)

OTHER PUBLICATIONS

21 C.F.R. §175.300 Resinous and Polymeric Coatings: Retrieved on Apr. 19, 2006. Retrieved from Internet: <URL: http://a257.g.akamaitech.net/7/257/2422/01apr20051500/edocket.access.gpo.gov/cfr_2005 . . .> (27 pages).

(Continued)

Primary Examiner — Thao T Tran

(57) ABSTRACT

A polymer useful in coating compositions is described. The polymer is preferably an unsaturated polyurethane polymer, which preferably has an iodine value of at least 10. The polymer may be combined with one or more liquid carriers to form a liquid coating composition useful in coating a variety of substrates, including planar metal substrates.

15 Claims, No Drawings

(56) References Cited

U.S. PATENT DOCUMENTS

| | | | |
|---|---|---|---|
| 3,368,988 A * | 2/1968 | Sekmakas | 528/245.5 |
| 3,377,406 A | 4/1968 | Newey et al. | |
| 3,390,206 A | 6/1968 | Thompson et al. | |
| 3,477,990 A | 11/1969 | Dante et al. | |
| 3,479,310 A | 11/1969 | Deiterich et al. | |
| 3,547,881 A | 12/1970 | Mueller et al. | |
| 3,547,885 A | 12/1970 | Dante et al. | |
| 3,694,407 A | 9/1972 | Krikorian | |
| 3,738,862 A | 6/1973 | Klarquist et al. | |
| 3,810,859 A | 5/1974 | Mikofalvy | |
| 3,862,914 A | 1/1975 | Anderson et al. | |
| 3,880,793 A | 4/1975 | Nakayama | |
| 3,933,706 A | 1/1976 | Momiyama et al. | |
| 3,943,187 A | 3/1976 | Wu | |
| 3,948,855 A | 4/1976 | Perry | |
| 3,969,300 A | 7/1976 | Nagata et al. | |
| 3,991,216 A | 11/1976 | Christenson et al. | |
| 3,997,694 A | 12/1976 | Wu | |
| 4,021,396 A | 5/1977 | Wu | |
| 4,028,294 A | 6/1977 | Brown et al. | |
| 4,033,920 A | 7/1977 | Isozaki et al. | |
| 4,048,141 A | 9/1977 | Doorakian et al. | |
| 4,064,087 A | 12/1977 | Das | |
| 4,076,676 A | 2/1978 | Sommerfeld | |
| 4,100,127 A | 7/1978 | Fukusaki et al. | |
| 4,122,052 A | 10/1978 | Aihara et al. | |
| 4,144,155 A | 3/1979 | Araki et al. | |
| 4,147,679 A | 4/1979 | Scriven et al. | |
| 4,151,143 A | 4/1979 | Blank et al. | |
| 4,212,776 A | 7/1980 | Martinez et al. | |
| 4,212,781 A | 7/1980 | Evans et al. | |
| 4,247,439 A | 1/1981 | Matthews et al. | |
| 4,247,659 A | 1/1981 | Sekmakes et al. | |
| 4,285,847 A | 8/1981 | Ting | |
| 4,289,674 A | 9/1981 | Christenson et al. | |
| 4,289,811 A | 9/1981 | Shelley, Jr. | |
| 4,294,737 A | 10/1981 | Sekmakes et al. | |
| 4,296,011 A | 10/1981 | Sekmakes et al. | |
| 4,303,488 A | 12/1981 | Seiler et al. | |
| 4,304,701 A | 12/1981 | Das et al. | |
| 4,337,185 A | 6/1982 | Wessling et al. | |
| 4,370,446 A | 1/1983 | Toyoda et al. | |
| 4,404,336 A | 9/1983 | Sekmakes et al. | |
| 4,413,015 A | 11/1983 | Anderson et al. | |
| 4,423,165 A | 12/1983 | Harper et al. | |
| 4,425,451 A | 1/1984 | Sekmakes et al. | |
| 4,440,897 A | 4/1984 | Maska | |
| 4,442,246 A | 4/1984 | Brown et al. | |
| 4,443,568 A | 4/1984 | Woo | |
| 4,444,923 A | 4/1984 | McCarty | |
| 4,446,258 A | 5/1984 | Chu et al. | |
| 4,461,857 A | 7/1984 | Sekmakes et al. | |
| 4,476,262 A | 10/1984 | Chu et al. | |
| 4,477,609 A | 10/1984 | Aluotto et al. | |
| 4,480,058 A | 10/1984 | Ting et al. | |
| 4,482,673 A | 11/1984 | Brown et al. | |
| 4,487,861 A | 12/1984 | Winner | |
| 4,497,946 A | 2/1985 | Sekmakes et al. | |
| 4,501,831 A | 2/1985 | Chu et al. | |
| 4,507,425 A | 3/1985 | Weaver | |
| 4,507,430 A * | 3/1985 | Shimada et al. | 524/839 |
| 4,539,348 A | 9/1985 | Gajria et al. | |
| 4,546,014 A | 10/1985 | Gajria et al. | |
| 4,560,714 A | 12/1985 | Gajria et al. | |
| 4,572,610 A | 2/1986 | Krajewski | |
| 4,579,888 A | 4/1986 | Kodama et al. | |
| 4,585,814 A | 4/1986 | Sekmakes et al. | |
| 4,600,737 A | 7/1986 | Georgalas et al. | |
| 4,623,680 A | 11/1986 | Azarnia et al. | |
| 4,629,491 A | 12/1986 | Swerdloff et al. | |
| 4,638,020 A | 1/1987 | Christenson et al. | |
| 4,644,030 A | 2/1987 | Loewrigkeit et al. | |
| 4,647,612 A | 3/1987 | Ranka et al. | |
| 4,683,273 A | 7/1987 | Bode | |
| 4,691,002 A | 9/1987 | Hegemann et al. | |
| 4,692,491 A | 9/1987 | Ranka et al. | |
| 4,703,071 A | 10/1987 | Owens | |
| 4,741,961 A | 5/1988 | Frisch et al. | |
| 4,871,810 A | 10/1989 | Saltman | |
| 4,898,911 A | 2/1990 | Miyashita et al. | |
| 4,943,359 A | 7/1990 | Patzschke et al. | |
| 4,946,911 A | 8/1990 | Treybig | |
| 4,963,602 A | 10/1990 | Patel | |
| 4,997,865 A | 3/1991 | Scherping et al. | |
| 5,051,470 A | 9/1991 | Woo et al. | |
| 5,068,266 A | 11/1991 | Kojima et al. | |
| 5,082,842 A | 1/1992 | Widmer | |
| 5,093,392 A | 3/1992 | Woo et al. | |
| 5,096,992 A | 3/1992 | Ross et al. | |
| 5,116,888 A | 5/1992 | Woo et al. | |
| 5,157,078 A | 10/1992 | Woo et al. | |
| 5,166,289 A | 11/1992 | Yezrielev et al. | |
| 5,173,526 A | 12/1992 | Vijayendran et al. | |
| 5,177,129 A | 1/1993 | Bobo, Jr. | |
| 5,196,481 A | 3/1993 | Owens et al. | |
| 5,201,436 A | 4/1993 | Owens et al. | |
| 5,212,241 A | 5/1993 | Woo et al. | |
| 5,252,637 A | 10/1993 | Craun et al. | |
| 5,252,669 A | 10/1993 | Maska et al. | |
| 5,264,469 A | 11/1993 | Mysliwczyk et al. | |
| 5,270,356 A | 12/1993 | Katamota et al. | |
| 5,290,828 A | 3/1994 | Craun et al. | |
| 5,296,525 A | 3/1994 | Spencer | |
| 5,342,864 A | 8/1994 | Craun et al. | |
| 5,344,858 A | 9/1994 | Hart et al. | |
| 5,360,863 A | 11/1994 | Meixner et al. | |
| 5,387,625 A | 2/1995 | Parekh et al. | |
| 5,428,084 A | 6/1995 | Swarup et al. | |
| 5,464,885 A | 11/1995 | Craun | |
| 5,500,463 A | 3/1996 | Nishimura et al. | |
| 5,504,145 A | 4/1996 | Treasurer | |
| 5,508,325 A | 4/1996 | Craun et al. | |
| 5,527,840 A | 6/1996 | Chutko et al. | |
| 5,532,297 A | 7/1996 | Woo et al. | |
| 5,554,671 A | 9/1996 | Craun et al. | |
| 5,576,063 A | 11/1996 | Briggs et al. | |
| 5,576,361 A | 11/1996 | Craun | |
| 5,672,653 A | 9/1997 | Frisch et al. | |
| 5,686,511 A | 11/1997 | Bobo | |
| 5,723,555 A | 3/1998 | Swarup et al. | |
| 5,733,970 A | 3/1998 | Craun | |
| 5,739,215 A | 4/1998 | Westerhof et al. | |
| 5,767,175 A | 6/1998 | Kamekura et al. | |
| 5,780,532 A | 7/1998 | Noda et al. | |
| 5,792,804 A | 8/1998 | Cibura et al. | |
| 5,830,952 A | 11/1998 | Pedersen et al. | |
| 5,840,384 A | 11/1998 | Noda et al. | |
| 5,869,552 A | 2/1999 | Pedersen et al. | |
| 5,869,568 A | 2/1999 | Maeda | |
| 5,877,239 A | 3/1999 | Craun et al. | |
| 5,898,049 A | 4/1999 | Müller et al. | |
| 5,907,012 A | 5/1999 | Voss et al. | |
| 5,922,817 A | 7/1999 | Pedersen et al. | |
| 5,939,482 A | 8/1999 | Kriessmann et al. | |
| 5,942,563 A | 8/1999 | DeGraaf | |
| 5,962,620 A | 10/1999 | Reich et al. | |
| 5,972,432 A | 10/1999 | Chutko et al. | |
| 5,976,615 A | 11/1999 | Menovcik et al. | |
| 5,976,700 A | 11/1999 | Chutko et al. | |
| 5,993,972 A | 11/1999 | Reich et al. | |
| 6,008,273 A | 12/1999 | Leibelt et al. | |
| 6,040,062 A | 3/2000 | McGee et al. | |
| 6,046,256 A | 4/2000 | Nakamura et al. | |
| 6,048,924 A | 4/2000 | Obayashi et al. | |
| 6,083,585 A | 7/2000 | Cahill et al. | |
| 6,087,417 A | 7/2000 | Stevenson et al. | |
| 6,126,999 A | 10/2000 | Tomasino et al. | |
| 6,136,927 A | 10/2000 | Swarup et al. | |
| 6,262,217 B1 | 7/2001 | Tallmadge et al. | |
| 6,300,428 B1 | 10/2001 | Stevenson et al. | |
| 6,306,934 B1 | 10/2001 | Bode et al. | |
| 6,339,125 B1 | 1/2002 | Bechara et al. | |
| 6,346,307 B1 | 2/2002 | Al Ghatta et al. | |
| 6,359,062 B1 | 3/2002 | Mallen et al. | |

(56) References Cited

U.S. PATENT DOCUMENTS

| | | |
|---|---|---|
| 6,429,254 B2 | 8/2002 | Schafheutle et al. |
| 6,465,559 B1 | 10/2002 | Bechara et al. |
| 6,514,619 B2 | 2/2003 | Shimada et al. |
| 6,576,689 B2 | 6/2003 | Noda et al. |
| 6,627,316 B1 | 9/2003 | Matsuki et al. |
| 6,730,361 B2 | 5/2004 | Parekh et al. |
| 6,831,136 B2 | 12/2004 | Chao et al. |
| 7,189,787 B2 | 3/2007 | O'Brien et al. |
| 7,375,174 B2 | 5/2008 | Ramesh et al. |
| 7,459,167 B1 | 12/2008 | Sengupta et al. |
| 7,479,519 B2 | 1/2009 | Krishnan |
| 7,534,830 B2 | 5/2009 | Williams |
| 7,592,047 B2 | 9/2009 | O'Brien et al. |
| 7,763,323 B2 | 7/2010 | Mayr et al. |
| 8,092,876 B2 | 1/2012 | O'Brien et al. |
| 8,142,868 B2 | 3/2012 | O'Brien et al. |
| 8,663,765 B2 | 3/2014 | Skillman et al. |
| 8,747,979 B2 * | 6/2014 | Cavallin et al. ............ 428/36.91 |
| 8,840,966 B2 * | 9/2014 | Cavallin et al. ............ 427/388.2 |
| 9,061,798 B2 * | 6/2015 | Cavallin et al. |
| 2003/0069380 A1 | 4/2003 | Flat et al. |
| 2004/0167252 A1 | 8/2004 | Melchiors et al. |
| 2005/0084686 A1 | 4/2005 | Imaizumi |
| 2005/0182155 A1 | 8/2005 | O'Dell et al. |
| 2005/0192400 A1 | 9/2005 | Killilea et al. |
| 2007/0027249 A1 | 2/2007 | Killilea |
| 2007/0031679 A1 | 2/2007 | Ushida et al. |
| 2008/0009601 A1 | 1/2008 | Killilea et al. |
| 2008/0166485 A1 | 7/2008 | Steenwinkel et al. |
| 2010/0183835 A1 | 7/2010 | O'Brien et al. |

FOREIGN PATENT DOCUMENTS

| | | | |
|---|---|---|---|
| EP | 0807647 A1 | 11/1997 | |
| EP | 0964031 A2 | 12/1999 | |
| EP | 2042535 A1 | 4/2009 | |
| GB | 1513866 | 6/1978 | |
| GB | 2152065 A | 7/1985 | |
| JP | 53097083 | 8/1978 | |
| JP | 6112746 | 1/1986 | |
| JP | 5043830 | 2/1993 | |
| JP | 673308 | 3/1994 | |
| JP | 10158528 | 3/1994 | |
| JP | 10139839 | 5/1998 | |
| JP | 2002138245 | 5/2002 | |
| JP | 2002155234 | 5/2002 | |
| JP | 2006077049 | 3/2003 | |
| JP | 2003321646 | 11/2003 | |
| JP | 2004026913 | 1/2004 | |
| JP | 2005089716 | 4/2005 | |
| JP | 2005179491 | 7/2005 | |
| JP | 2007031726 A * | 2/2007 | ............ C08L 75/04 |
| JP | 2007238698 | 9/2007 | |
| JP | 2008297379 | 12/2008 | |
| WO | 9308154 A1 | 4/1993 | |
| WO | 9732930 A1 | 9/1997 | |
| WO | 0192366 A1 | 12/2001 | |
| WO | 03076530 A2 | 9/2003 | |
| WO | 2004055086 A1 | 7/2004 | |
| WO | 2004090020 A1 | 10/2004 | |
| WO | 2006045017 A1 | 4/2006 | |
| WO | 2007066816 A1 | 6/2007 | |
| WO | 2008036629 A2 | 3/2008 | |
| WO | 2010062928 A1 | 6/2010 | |
| WO | 2010066902 A1 | 6/2010 | |

OTHER PUBLICATIONS

ASTM International, Designation: D 1200-94 (Reapproved 2005), Standard Test Method for Viscosity by Ford Viscosity Cup, Published Jun. 2005 (4 pages).

ASTM International, Designation: D 2196-05, Standard Test Methods for Rheological Properties of Non-Newtonian Materials by Rotational (Brookfield type) Viscometer, Published Aug. 2005 (5 pages).

ASTM International, Designation: D 3359-02, Standard Test Methods for Measuring Adhesion by Tape Test, Published Oct. 2002 (7 pages).

ASTM International, Designation: D 5402-93 (Reapproved 1999), Standard Practice for Assessing the Solvent Resistance of Organic Coatings Using Solvent Rubs, Published Jul. 1993 (3 pages).

Chattopadhyay, et al., "Effect of Chain Extender on Phase Mixing and Coating Properties of Polyurethane Ureas," Ind. Eng. Chem. Res., 2005, vol. 44, p. 1772-1779 (8 pages).

Guidelines for Industry, "Preparation of Food Contact Notifications and Food Additive Petitions for Food Contact Substances: Chemistry Recommendations," Center for Food Safety and Applied Nutrition, Apr. 2002, Retrieved on Apr. 19, 2006. Retrieved from Internet: <URL: http://www.cfsan.fda.gov/~dms/opa2pmnc.html> (37 pages).

Niangui, et al., "Synthesis of Glycidyl Methacrylate," Thermosetting Resin, Jan. 2002, vol. 17, No. 1, p. 27-28, (2 pages) [English-language abstract at p. 28].

Szycher, et al., "Development of an Aliphatic Biomedical-Grade Polyurethane Elastomer," Journal of Elastomers and Plastics, 1983, vol. 15, p. 81-95 (16 pages).

Pytela Jindrich and Sufcak Miloslav "Polybutadiene-urethane Elastomers with Outstanding Resistance to Aggressive Aqueous Media", Paper 9 (7 Pages).

International Search Report and Written Opinion for PCT/US2010/049356 mailed on Dec. 7, 2010 (11 pages).

International Standard, IDS 3961, Animal and Vegetable Fats and Oils—Determination of Iodine Value; Fourth Edition Apr. 1, 2009.

Document entitled "Polybutadiene", (4Pages).

Hein, Richard W. "Driers for Waterborne Coatings", Journal of Coatings Technology, vol. 70, No. 866, Nov. 1998, pp. 19-22.

ASTM International, Designation: D 5768-02 (Reapproved 2006) Standard Test Method for Determination of Iodine Value of Tall Oil Fatty Acids. Published Nov. 2009. (3 Pages).

Paquot, et al. Standard Methods for the Analysis of Oils, Fats and Derivatives, $7^{th}$ Revised and Enlarged Edition. (8 Pages).

* cited by examiner

POLYURETHANE COATING COMPOSITION

CROSS-REFERENCE TO RELATED APPLICATION(S)

This application is a continuation of U.S. application Ser. No. 13/496,758 filed on Mar. 16, 2012 and entitled "POLYURETHANE COATING COMPOSITION," which is the National Stage filing under 35 U.S.C. 371 of International Application No. PCT/US2010/049356 filed on Sep. 17, 2010 and entitled "POLYURETHANE COATING COMPOSITION," which claims the benefit of U.S. Provisional Patent Application No. 61/300,647 filed on Feb. 2, 2010 and entitled "POLYURETHANE COATING COMPOSITION," and is a continuation-in-part of International Application No PCT/US2010/042254 filed on Jul. 16, 2010, and entitled "COATING COMPOSITION AND ARTICLES COATED THEREWITH." International Application No. PCT/US2010/042254 claims the benefit of U.S. Provisional Application No. 61/243,888 filed Sep. 18, 2009 and entitled "COATING COMPOSITION AND ARTICLES COATED THEREWITH." The disclosure of each of the applications referenced above is incorporated herein by reference in its entirety.

TECHNICAL FIELD

This invention relates to a polymer coating composition. In particular, the present invention relates to a polymer coating composition useful in coating metal substrates.

BACKGROUND

Polymer coating compositions are routinely applied to substrates, especially metal substrates. Such coatings are used for a variety of reasons, including, for example, to protect the substrate from degradation, to beautify the substrate (e.g., to provide color, brightness, etc.), and/or to reflect light.

Many such polymer coating compositions are applied on planar substrate (e.g., using a coil coating process) that is subsequently formed into a finished article. The designer of such coatings is faced with a multitude of challenges in developing suitable coatings. For example, coating compositions are desired that perform well when applied to a variety of different types of metals, which may have differing surface characteristics and differing levels of cleanliness. In general, it is desired that the coatings adhere well to a variety of different substrates; exhibit suitable flexibility, hardness, and abrasion resistance (e.g., to endure fabrication steps that may be required to form a finished article); and exhibit suitable aesthetic qualities. Achieving a suitable balance of coating properties at a suitably low cost can be difficult because, oftentimes, improvements made to one coating property are associated with degradation of another coating property. For example, improved coating hardness is often achieved to the detriment of coating flexibility.

Accordingly, there is a continuing need for coating compositions that exhibit one or more enhanced coating properties.

SUMMARY

The present invention provides a polymer useful in coating applications.

In one embodiment, the polymer is an unsaturated polymer, more preferably an unsaturated polyurethane polymer, and even more preferably an unsaturated polyurethane polymer having an iodine value of at least 10. The unsaturated polymer preferably includes one or more aliphatic carbon-carbon double bonds, and more preferably includes one or more "reactive" aliphatic carbon-carbon double bonds such as, for example, a vinylic double bond, a conjugated double bond, a double bond present in a strained ring group, a double bond present in an unsaturated bicyclic group, or a combination thereof.

In another embodiment, the polymer is an unsaturated polymer, more preferably an unsaturated polyurethane polymer, and even more preferably an unsaturated polyurethane polymer having an iodine value of at least 10, which includes one or more unsaturated segments formed from a (poly)alkene compound, more preferably a functionalized polybutadiene-containing compound. The unsaturated polymer preferably includes at least 5% by weight of the (poly)alkene compound, and more preferably at least 5% by weight of functionalized polybutadiene-containing compound.

The present invention also provides a coating composition that includes an unsaturated polymer described herein. The coating composition preferably includes one or more optional liquid carriers. Suitable liquid carriers may include one or more organic solvents, water, or a combination thereof.

The present invention also provides a coated article. In one embodiment, the coated article has a metal substrate where at least a portion of the metal substrate is coated with a coating composition described herein.

The present invention further provides a method for forming a coated article. The method typically includes applying a coating to at least a portion of a planar metal substrate. The coating composition preferably includes a film-forming amount of an unsaturated polymer of the present invention (preferably an unsaturated polyurethane polymer) and one or more optional liquid carriers. The coated metal substrate is preferably heated to form a cured coating, which is preferably a crosslinked coating. The coated metal substrate is preferably heated to a peak metal temperature of at least about 350° F. (177° C.).

The above summary of the present invention is not intended to describe each disclosed embodiment or every implementation of the present invention. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

The details of one or more embodiments of the present invention are set forth in the description below. Other features, objects, and advantages of the present invention will be apparent from the description and from the claims.

SELECTED DEFINITIONS

Unless otherwise specified, the following terms as used herein have the meanings provided below.

A group that may be the same or different is referred to as being "independently" something. Substitution is anticipated on the organic groups of the compounds of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, Si, or S atoms, for example, in the chain (as in an alkoxy group) as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like. As used herein, the term "group" is intended to be a recitation of both the particular moiety, as well as a recitation of the broader class of substituted and unsubstituted structures that includes the moiety.

The term "substantially free" of a particular mobile compound means that the compositions of the present invention contain less than 1,000 parts per million (ppm) of the recited mobile compound. The term "essentially free" of a particular mobile compound means that the compositions of the present invention contain less than 100 ppm of the recited mobile compound. The term "essentially completely free" of a particular mobile compound means that the compositions of the present invention contain less than 5 ppm of the recited mobile compound. The term "completely free" of a particular mobile compound means that the compositions of the present invention contain less than 20 parts per billion (ppb) of the recited mobile compound. If the aforementioned phrases are used without the term "mobile" (e.g., "substantially free of XYZ compound") then the compositions of the present invention contain less than the aforementioned amount of the compound whether the compound is mobile in the coating or bound to a constituent of the coating.

The term "crosslinker" refers to a molecule capable of forming a covalent linkage between polymers or between two different regions of the same polymer.

The terms "self-crosslinking" or "self-crosslinkable," when used in the context of a self-crosslinking polymer, refers to the capacity of a polymer to enter into a crosslinking reaction with itself and/or another molecule of the polymer, in the absence of an external crosslinker, to form a covalent linkage therebetween. Typically, this crosslinking reaction occurs through reaction of complementary reactive functional groups present on the self-crosslinking polymer itself or two or more separate molecules of the self-crosslinking polymer.

The term "water-dispersible" in the context of a water-dispersible polymer means that the polymer can be mixed into water (or an aqueous carrier) to form a stable mixture. For example, a mixture that readily separates into immiscible layers is not a stable mixture. The term "water-dispersible" is intended to include the term "water-soluble." In other words, by definition, a water-soluble polymer is also considered to be a water-dispersible polymer.

The term "dispersion" in the context of a dispersible polymer refers to the mixture of a dispersible polymer and a carrier. The term "dispersion" is intended to include the term "solution."

The term "on," when used in the context of a coating applied on a substrate, includes both coatings applied directly or indirectly to the substrate. Thus, for example, a coating applied to a primer layer overlying a substrate constitutes a coating applied on the substrate.

The term "polymer" includes both homopolymers and copolymers (i.e., polymers of two or more different monomers). Similarly, the term "polyurethane polymer" is intended to include both homopolymers and copolymers (e.g., polyester-urethane polymers).

The term "aliphatic" when used in the context of a carbon-carbon double bond includes both linear (or open chain) aliphatic carbon-carbon double bonds and cycloaliphatic carbon-carbon double bonds, but excludes aromatic carbon-carbon double bonds of aromatic rings.

The term "unsaturation" when used in the context of a compound refers to a compound that includes at least one non-aromatic (i.e., aliphatic) carbon-carbon double bond.

The term "vinyl polymer" refers to a polymer prepared by addition polymerizing an ethylenically unsaturated component (e.g., a mixture of ethylenically unsaturated monomers and/or oligomers).

The term "(meth)acrylate" includes both acrylates and methacrylates.

The term "polycyclic" when used in the context of a group refers to an organic group that includes at least two cyclic groups in which one or more atoms (and more typically two or more atoms) are present in the rings of both of the at least two cyclic groups. Thus, for example, a group that consists of two cyclohexane groups connected by a single methylene group is not a polycyclic group.

The term "comprises" and variations thereof do not have a limiting meaning where these terms appear in the description and claims.

The terms "preferred" and "preferably" refer to embodiments of the present invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the present invention.

As used herein, "a," "an," "the," "at least one," and "one or more" are used interchangeably. Thus, for example, a coating composition that comprises "an" additive can be interpreted to mean that the coating composition includes "one or more" additives.

Also herein, the recitations of numerical ranges by endpoints include all numbers subsumed within that range (e.g., 1 to 5 includes 1, 1.5, 2, 2.75, 3, 3.80, 4, 5, etc.). Furthermore, disclosure of a range includes disclosure of all subranges included within the broader range (e.g., 1 to 5 discloses 1 to 4, 1.5 to 4.5, 1 to 2, etc.).

DETAILED DESCRIPTION

In one aspect, the present invention provides a coating composition useful in a variety of applications. The coating composition is useful for forming an adherent coating on various metal substrates and is particularly suited for use in metal coil coating applications. In preferred embodiments, the coating composition includes an unsaturated polyurethane binder polymer that is preferably present in a film-forming amount. The unsaturated polyurethane polymer preferably includes at least one aliphatic carbon-carbon double bond, and more preferably includes a plurality of aliphatic carbon-carbon double bonds. While not intending to be bound by any theory, the inclusion of an efficacious amount of aliphatic carbon-carbon double bonds in the polyurethane polymer of the present invention has been observed to yield a desirable balance of coating properties such as good coating hardness, good chemical resistance, and good coating flexibility, which is believed to be attributable, at least in part, to the formation of crosslinks through the aliphatic carbon-carbon double bonds upon coating cure.

In certain preferred embodiments, at least some of the aliphatic carbon-carbon double bonds are "reactive" carbon-carbon double bonds that are preferably sufficiently reactive under typical coating cure conditions (more preferably coil coating cure conditions) to participate in a reaction with one or more other functionalities present in the coating composition to form a covalent linkage. Non-limiting examples of reactive aliphatic carbon-carbon double bonds include vinylic double bonds (e.g., —C($R_1$)=C($R_2R_3$)), conjugated aliphatic double bonds (e.g., —C($R_4$)=C($R_5$)—C($R_6$)=C($R_7$)—), aliphatic double bonds present in strained ring groups, aliphatic double bonds present in certain unsaturated polycyclic groups (e.g., polycyclic groups including an unsaturated bridged bicyclic group), and combinations thereof (In the above representative structural formulas, $R_1$ preferably denotes a hydrogen atom, a halogen atom, or a methyl group; $R_2$ and $R_3$ preferably each independently denote a hydrogen or halogen atom; and $R_4$ to $R_7$ preferably each independently denote a hydrogen atom, a halogen atom, or an organic group such as, for example, a methyl group, a substituted or unsubstituted alkyl group, a substituted or unsubstituted cycloalkyl group, a substituted or unsubstituted aryl group, or a substituted or unsubstituted alkenyl or alkynyl group.)

Heat of hydrogenation may be a useful indicator of the reactivity of an aliphatic carbon-carbon double bond. In some embodiments, the unsaturated binder polymer includes one or more aliphatic carbon-carbon double bonds having a heat of hydrogenation greater than that of cyclohexene. Such aliphatic carbon-carbon double bonds may be present in either an open chain portion of the polymer or in a cyclic group of the polymer. In certain embodiments, the unsaturated binder polymer includes one or more aliphatic carbon-carbon double bonds having a heat of hydrogenation that is at least about as high as that of bicyclo[2.2.2]octene (e.g., −28.25 kcal/mole), and more preferably, at least about as high as that of bicyclo[2.2.1]heptene (e.g., −33.13 kcal/mole). As used herein, when a heat of hydrogenation is stated to be, for example, "at least X," "greater than X," or the like, it should be understood that reference is made to the absolute value of the heat of hydrogenation because heats of hydrogenation are typically reported as negative values, with a larger negative value indicating a higher heat of hydrogenation (e.g., −40 kcal/mole is a higher heat of hydrogenation than −10 kcal/mole).

The unsaturated polyurethane polymer of the present invention may include any suitable number of aliphatic carbon-carbon double bonds. Iodine value is a useful measure of the number of aliphatic carbon-carbon double bonds present in a material. The unsaturated polyurethane polymer of the present invention may have any suitable iodine value to achieve a desired result. In preferred embodiments, the unsaturated polyurethane polymer has an iodine value of at least about 10, more preferably at least about 20, even more preferably at least about 35, and optimally at least about 50. The upper range of suitable iodine values is not particularly limited, but in most embodiments the iodine value typically will not exceed about 100 or about 120. The aforementioned iodine values are expressed in terms of the centigrams of iodine per gram of the material. Iodine values may be determined, for example, using ASTM D 5768-02 (Reapproved 2006) entitled "Standard Test Method for Determination of Iodine Values of Tall Oil Fatty Acids." In certain embodiments, the total polyurethane content of the coating composition exhibits an average iodine value pursuant to the aforementioned values.

In some embodiments, at least a substantial portion (e.g., greater than 5%, greater than 10%, greater than 25%, greater than 50%, etc.) of the aforementioned iodine values for the unsaturated polyurethane polymer is attributable to the presence of one or more of: vinylic carbon-carbon double bonds, conjugated aliphatic carbon-carbon double bonds, aliphatic carbon-carbon double bonds present in strained ring groups, aliphatic carbon-carbon double bonds present in unsaturated bicyclic groups, and combinations thereof. In certain embodiments, of the total measured iodine value for the unsaturated polyurethane polymer, at least about 10, preferably at least about 20, more preferably at least about 35, and optimally at least about 50 centigrams of iodine per gram of unsaturated polyurethane polymer is attributable to the presence of aliphatic carbon-carbon double bonds and more preferably to the presence of reactive aliphatic carbon-carbon double bonds.

In certain preferred embodiments, the unsaturated polyurethane polymer includes alkene and/or polyalkene groups (referred to collectively herein as "(poly)alkene" groups), more preferably one or more alkene and/or polyalkene moieties, having at least one aliphatic carbon-carbon double bond. In some embodiments, the (poly)alkene groups include at least some vinylic carbon-carbon double bonds and/or conjugated carbon-carbon double bonds. The (poly)alkene groups may be monovalent or polyvalent (e.g., divalent or trivalent), are preferably monovalent or divalent, and are even more preferably divalent.

The (poly)alkene groups may be substituted or unsubstituted and may be present as backbone and/or pendant groups. Non-limiting examples of suitable (poly)alkene groups include groups formed from functionalized butadiene or polybutadiene, unsaturated fatty acids (e.g., mono- or poly-unsaturated fatty acids such as arichidonic, eleostearic, erucic, licanic, linoleic, linolenic, oleic, palmitoleic, ricinoleic acid, and derivatives or mixtures thereof), polyisoprene, poly-EPDM (ethylene propylene diene monomer), modified poly-EPDM (e.g., modified with dicyclopentadiene, vinyl norbornene, etc.), or a combination thereof. Groups formed from fully hydrogenated polyalkene compounds, such as, for example, backbone segments formed from fully hydrogenated polybutadiene compounds, are not (poly)alkene groups.

As discussed above, in some embodiments, a functionalized (poly)alkene compound may be used as a reactant for forming the polyurethane of the present invention. The functionalized (poly)alkene compound may be monofunctional or polyfunctional (e.g., difunctional, trifunctional, etc.), preferably monofunctional or difunctional, more preferably difunctional. Suitable functional groups may include any of the functional groups described herein, including, for example, reactive hydrogen groups.

Unsaturated polybutadiene-containing groups, and unsaturated polybutadiene backbone segments in particular, are preferred (poly)alkene groups. Hydroxyl-terminated polybutadiene is a presently preferred compound for incorporating (poly)alkene groups into the polyurethane polymer of the present invention. Functionalized polybutadiene-containing compounds such as hydroxylated polybutadiene are commercially available. Non-limiting examples of commercial functionalized polybutadiene materials include the POLY BD R45HTLO, POLY BD R20LM, KRASOL LBH 2000, KRASOL LBH 2040, KRASOL LBH 3000, KRASOL LBH 5000, KRASOL LBH 10000, KRASOL LBH-P 2000, KRASOL LBH-P 3000, and KRASOL LBH-P 5000 products (all available from Cray Valley). Preferred functionalized polybutadiene-containing compounds have a number average molecular weight ("Mn") of from about 500 to about 10,000, more preferably from about 1,000 to about 5,000, and even more preferably from about 2,000 to about 3,000.

When present in the unsaturated polyurethane, the (poly) alkene groups are preferably present in an amount of at least about 1 weight percent ("wt-%"), more preferably at least about 5 wt-%, and even more preferably at least about 15 wt-%, based on the total weight of the unsaturated polyurethane polymer. The (poly)alkene groups are preferably included in an amount of less than about 80 wt-%, more preferably less than about 50 wt-%, and even more preferably less than about 20 wt-%, based on the total weight of the unsaturated polyurethane polymer. The above weight percentages are based on the amount of (poly)alkene-group-containing compounds used to form the polyurethane polymer.

As previously discussed, in some embodiments, the unsaturated binder polymer of the present invention includes one or more polycylic groups, and more preferably one or more strained polycyclic groups such as, for example, an unsaturated bridged bicyclic group. In some embodiments, the unsaturated polyurethane polymer includes one or more unsaturated bicyclic structures represented by the IUPAC (International Union of Pure and Applied Chemistry) nomenclature of Expression (I) below:

bicyclo[$x.y.z$]alkene

In Expression (I),
x is an integer having a value of 2 or more,
y is an integer having a value of 1 or more,
z is an integer having a value of 0 or more, and
the term alkene refers to the IUPAC nomenclature designation (e.g., hexene, heptene, heptadiene, octene, etc.) for a given bicyclic molecule and denotes that the bicyclic group includes one or more double bonds (e.g. $\geq 1$, $\geq 2$, $\geq 3$ double bonds).

Preferably z in Expression (I) is 1 or more. In other words, preferred bicyclic groups include a bridge with a least one atom (typically one or more carbon atoms) interposed between a pair of bridgehead atoms, where the at least one atom is shared by at least two rings. By way of example, bicyclo[4.4.0]decane does not include such a bridge.

Preferably, x has a value of 2 or 3 (more preferably 2) and each of y and z independently have a value of 1 or 2.

Non-limiting examples of some suitable unsaturated bicyclic groups represented by Expression (I) include monovalent or polyvalent (e.g., divalent) variants of bicyclo[2.1.1] hexene, bicyclo[2.2.1]heptene (i.e., norbornene), bicyclo [2.2.2]octene, bicyclo[2.2.1]heptadiene, and bicyclo[2.2.2] octadiene. Bicyclo[2.2.1]heptene is a presently preferred unsaturated bicyclic group. Suitable unsaturated bridged bicyclic groups may also include Diels-Alder adducts of maleic anhydride and rosin (see, e.g., U.S. Pat. No. 5,212, 213 for further discussion of such adducts).

It is contemplated that the unsaturated bicyclic groups represented by Expression (I) may contain one or more heteroatoms (e.g., nitrogen, oxygen, sulfur, etc.) and may be substituted to contain one or more additional substituents. For example, one or more cyclic groups (including, e.g., pendant cyclic groups and ring groups fused to a ring of the bicyclic group) or acyclic groups may be attached to the bicyclic group represented by Expression (I). Thus, for example, in some embodiments the bicyclic group of Expression (I) may be present in a tricyclic or higher polycyclic group.

Non-limiting examples of suitable unsaturated strained ring groups (other than those that may be present in an unsaturated bridged bicyclic group) may include substituted or unsubstituted, monovalent or polyvalent (e.g., divalent) variants of the following: cyclopropene (e.g., 1,2-dimethylcyclopropene), ethylidenecyclopropane, cyclobutene, methylenecyclobutane, trans-cyclooctene, trans-cyclononene, cyclobutadiene, cyclopentadiene, 1,3-cyclohexadiene, 1,3-cycloheptadiene, 1,3-cyclooctadiene, 1,3-cyclononadiene, and 1,3-cyclodecadiene, and derivatives and combinations thereof. By way of example, a cyclohexene group is not typically considered to be a strained ring group. In the context of monocyclic ring systems, rings including 3 to 5 atoms, and especially 3 or 4 atoms, tend to exhibit the greatest amount of total ring strain. Examples of such strained monocylic ring systems are included in the above list.

The unsaturated polyurethane polymer preferably includes a sufficient number of urethane linkages to provide the desired coating properties for the desired end use. Such coating properties may include flexibility, abrasion resistance, and/or fabrication (e.g., to accommodate stamping processes used to form articles from coated planar metal substrate). Preferred unsaturated polyurethane polymers preferably include on average at least about 2 urethane linkages, more preferably at least about 10 urethane linkages, and even more preferably at least about 20 urethane linkages per molecule of the polymer. While the number of urethane linkages present in the unsaturated polyurethane polymer is not particularly restricted on the high end and may vary depending upon molecular weight, in certain embodiments, the polyurethane polymer includes on average less than about 1,000 urethane linkages, less than about 200 urethane linkages, or less than about 50 urethane linkages per molecule of the polymer.

Isocyanate content may be another useful measure of the number of urethane linkages in a polymer. In presently preferred embodiments, the unsaturated polyurethane polymer is formed from reactants including, based on total nonvolatiles, at least about 0.1 wt-%, more preferably at least about 1 wt-%, and even more preferably at least about 5 wt-% of an isocyanate compound. The upper amount of suitable isocyanate compound concentration is not particularly limited and will depend upon the molecular weight of the one or more isocyanate compounds utilized as reactants. Typically, however, the unsaturated polyurethane polymer is formed from reactants including, based on total nonvolatiles, less than about 35 wt-%, more preferably less than about 30 wt-%, and even more preferably less than about 25 wt-% of an isocyanate compound. Preferably, the isocyanate compound is incorporated into a backbone of the unsaturated polyurethane polymer via a urethane linkage, and more preferably a pair of urethane linkages.

The unsaturated polyurethane polymer may include a backbone of any suitable structural configuration. The backbone may have different structural configurations depending on a variety of factors such as the materials used to form the backbone, cost, and the desired end use for the polymer. The backbone may optionally include one or more other backbone step-growth linkages (e.g., condensation linkages) such as, for example, amide, ester, carbonate ester, ether, imide, imine, urea linkages, or a combination thereof. Moreover, the backbone of the unsaturated polyurethane polymer may optionally include one or more oligomer or polymer segments selected from, for example, acrylic, epoxy, polyamide, polyester, poly(carbonate ester), polyether, polyimide, polyimine, polyurea, copolymer segments thereof, or a combination thereof.

In some embodiments, the polyurethane polymer is a linear polymer or a substantially linear, polymer. In other embodiments, the polyurethane polymer may include branching.

The polyurethane polymer of the present invention may have any suitable end groups and/or optional side groups.

The unsaturated polyurethane polymer of the present invention may be of any suitable molecular weight. In embodiments where the unsaturated polyurethane polymer is water-dispersible, the Mn of the polymer after optional chain extension, if any, is typically no greater than 500,000, more typically no greater than 100,000, and even more typically no greater than 40,000. In such embodiments, the Mn of the unsaturated polyurethane polymer after optional chain extension, if any, is preferably at least 5,000, more preferably at least 10,000, and even more preferably at least 30,000. The molecular weight of the polyurethane polymer in solvent-based coating embodiments may be similar to, or different from, that described above.

The coating composition of the present invention preferably includes at least about 5% by weight (wt-%), more preferably at least about 20 wt-%, even more preferably at least about 30 wt-%, and even more preferably at least about 45 wt-% of the unsaturated polyurethane polymer, based on the total weight of nonvolatile material in the coating composition. In some embodiments, the coating composition includes from about 50 to about 100 wt-% of unsaturated polyurethane polymer, based on the total weight of nonvolatile material in the coating composition. The upper amount of unsaturated polyurethane polymer included in the coating composition of the present invention is not especially limited. In some embodiments, the coating composition includes less than 100 wt-%, more preferably less than 95 wt-%, and even more preferably less than 85 wt-% of unsaturated polyurethane polymer, based on the total weight of nonvolatile material in the coating composition. In some embodiments, the coating composition includes less than about 50 wt-% of unsaturated polyurethane polymer, based on the total weight of nonvolatile material in the coating composition The unsaturated polyurethane polymer of the present invention may be formed using any suitable reactants and any suitable process. Polyurethane polymers are typically formed by reacting ingredients that include one or more polyols, one or more isocyanate-functional compounds, and optionally one or more additional reactants (e.g., organic materials having one or more active hydrogen groups). If desired, the polyurethane polymer may be formed through an optional polyurethane prepolymer intermediate. If such a prepolymer is used, the prepolymer may be optionally chain extended using one or more chain extender agents. Chain-extending techniques and materials (e.g., amine-functional chain extenders) such as those described in International Application No. PCT/US10/42254 can be used.

Any suitable polyol or mixture of polyols may be used to form the unsaturated polyurethane polymer of the present invention. The one or more polyols may be a monomer, an oligomer, a polymer, or a mixture thereof. In addition, the one or more polyols can be a diol, a triol, a polyol having 4 or more hydroxyl groups, or a mixture thereof. Diols are presently preferred. Non-limiting examples of suitable oligomer and/or polymer polyols include polyether polyols, polyester polyols, polyether-ester polyols, polyimide polyols, polyurea polyols, polyamide polyols, polycarbonate polyols, saturated or unsaturated polyolefin polyols, polyurethane polyols, and combinations thereof. Suitable polyol monomers may include, for example, glycols and/or glycerol.

A variety of isocyanate-functional compounds may be used to form the polyurethane polymer. In some embodiments, the isocyanates are incorporated into the polyurethane polymer predominantly or exclusively through urethane linkages. In other embodiments, at least some of the isocyanate compound may be incorporated into the backbone of the polyurethane polymer via one or more non-urethane step-growth linkages (e.g., urea) formed through a reaction involving an isocyanate group (—NCO) of the isocyanate compound.

The isocyanate compound may be any suitable compound, including an isocyanate compound having 1 isocyanate group; a polyisocyanate compound having 2, 3, or 4 or more isocyanate groups; or a mixture thereof. Suitable diisocyanates may include isophorone diisocyanate (i.e., 5-isocyanato-1-isocyanatomethyl-1,3,3-trimethylcyclohexane); 5-isocyanato-1-(2-isocyanatoeth-1-yl)-1,3,3-trimethylcyclohexane; 5-isocyanato-1-(3-isocyanatoprop-1-yl)-1,3,3-trimethylcyclohexane; 5-isocyanato-(4-isocyanatobut-1-yl)-1,3,3-trimethylcyclohexane; 1-isocyanato-2-(3-isocyanatoprop-1-yl)cyclohexane; 1-isocyanato-2-(3-isocyanatoeth-1-yl)cyclohexane; 1-isocyanato-2-(4-isocyanatobut-1-yl)cyclohexane; 1,2-diisocyanatocyclobutane; 1,3-diisocyanatocyclobutane; 1,2-diisocyanatocyclopentane; 1,3-diisocyanatocyclopentane; 1,2-diisocyanatocyclohexane; 1,3-diisocyanatocyclohexane; 1,4-diisocyanatocyclohexane; dicyclohexylmethane 2,4'-diisocyanate; trimethylene diisocyanate; tetramethylene diisocyanate; pentamethylene diisocyanate; hexamethylene diisocyanate; ethylethylene diisocyanate; trimethylhexane diisocyanate; heptamethylene diisocyanate; 2-heptyl-3,4-bis(9-isocyanatononyl)-1-pentyl-cyclohexane; 1,2-, 1,4-, and 1,3-bis(isocyanatomethyl)cyclohexane; 1,2-, 1,4-, and 1,3-bis(2-isocyanatoeth-1-yl)cyclohexane; 1,3-bis(3-isocyanatoprop-1-yl)cyclohexane; 1,2-, 1,4- or 1,3-bis(4-isocyanatobuty-1-yl) cyclohexane; liquid bis(4-isocyanatocyclohexyl)-methane; and derivatives or mixtures thereof.

In some embodiments, the isocyanate compounds are preferably non-aromatic. Non-aromatic isocyanates are particularly desirable for coating compositions intended for use on an interior surface (e.g., a food-contact surface) of a food or beverage can. Therefore, in certain embodiments, the polyurethane polymer of the present (and preferably the coating composition) does not contain any structural units derived from an aromatic isocyanate compound. Isophorone diisocyanate (IPDI) and hexamethylene diisocyanate (HMDI) are preferred non-aromatic isocyanates.

The reactants used to produce the unsaturated polyurethane polymer (e.g., one or more polyol and one or more isocyanate compounds) of the present invention may include any suitable ratio of isocyanate to hydroxyl groups. In some embodiments, the ratio of isocyanate to hydroxyl groups (NCO:OH) is preferably from 1.05:1 to 2:1, more preferably from 1.1:1 to 1.8:1, and even more preferably from 1.2:1 to 1.6:1.

In some embodiments, at least some, or alternatively all, of the one or more isocyanate compounds may be a partially blocked polyisocyanate. Certain embodiments may benefit from the inclusion of one or more blocked isocyanate groups (e.g., deblockable isocyanate groups) in the polyurethane polymer as a means for forming covalent linkages with other components of the coating composition, including, for example, the polyurethane polymer itself. Preferred partially blocked polyisocyanates contain, on average, at least about 1.5, more preferably at least about 1.8, and even more preferably at least about 2 free (or unblocked) isocyanate groups per molecule of partially blocked polyisocyanate and on average, at least about 0.5, more preferably at least about 0.7, and even more preferably at least about 1 blocked isocyanate groups (preferably deblockable isocyanate groups) per molecule of partially blocked polyisocyanate. For further discussion of suitable materials and methodologies relating to the use of partially blocked isocyanate compounds in forming polyurethane polymers see International Application Nos. PCT/US2009/065848 and PCT/US10/42254.

Aliphatic carbon-carbon double bonds may be incorporated in the unsaturated polyurethane polymer of the present invention using any suitable process. For example, one or more reactants including one or more aliphatic carbon-carbon double bonds can be included in the reactants used to form the polyurethane polymer. Alternatively, the polyurethane polymer may be post modified to include some, or all, of the aliphatic carbon-carbon double bonds. In some embodiments, the aliphatic carbon-carbon double bonds are incorporated into the polyurethane polymer via a step-growth reaction involving unsaturated monomers, oligomers, and/or polymers having one or more active hydrogen groups (e.g., such as those described herein). An unsaturated polyol is an example of one such reactant. In some embodiments, an addition reaction may be used to incorporate aliphatic carbon-carbon double bonds into the polyurethane polymer. For example, an unsaturated compound such as a polybutadiene compound may be incorporated into the polyurethane polymer itself, or another reactant used to form the polyurethane polymer (e.g. an unsaturated reactant having one or more active hydrogen groups), via an addition reaction such as a free-radical polymerization.

As previously discussed, in some embodiments, the unsaturated polyurethane polymer of the present invention includes one or more (poly)alkene groups. By way of example, the following reaction pathways may be used to incorporate the (poly)alkene groups into the polyurethane polymer: step-growth reactions (e.g., using a functionalized (poly)alkene-containing compound having one or more active hydrogen groups), free radical initiated reactions, Diels-Alder reactions, etc. Non-limiting examples of suitable groups for linking the (poly)alkene segment to one or more other portions of the polyurethane polymer include any of the linkage groups disclosed herein, including, for example, step-growth or addition (e.g., hydrocarbyl) linkages.

In some embodiments, the (poly)alkene group may be incorporated into the polymer via reaction of (i) one or more active hydrogen groups present in a compound containing the (poly)alkene group with (ii) a complementary active hydrogen group present on the polymer or a reactant used to form the polymer. Non-limiting examples of suitable active hydrogen groups include groups having a hydrogen attached to an oxygen (O), sulfur (S), and/or nitrogen (N) atom as in the groups =OH, —COOH, —SH, =NH, and $NH_2$. It is further contemplated that such reactions and/or linkage groups may also be used to incorporate any of the other aliphatic carbon-carbon double bond containing groups disclosed herein (e.g., unsaturated polycyclic groups, unsaturated strained ring groups, vinylic groups, etc.).

Below are some specific examples of methods for introducing (poly)alkene groups into the polyurethane polymer. It is also contemplated that similar such methods may be used to incorporate one or more other aliphatic carbon-carbon double bond containing groups disclosed herein.

1. A hydroxyl-functional (poly)alkene compound may be incorporated into the polyurethane polymer via reaction of the one or more hydroxyl groups with isocyanate and/or carboxylic acid groups present on the polyurethane polymer or a reactant used to form the polyurethane polymer.
2. A maleinized (poly)alkene (e.g., a (poly)alkene compound modified with maleic anhydride such as maleinized polybutadiene) may be incorporated into the polyurethane polymer via reaction of the acid groups/anhydride group with hydroxyl groups present on the polyurethane polymer or a reactant used to form the polyurethane polymer.
3. A maleinized (poly)alkene compound (e.g., maleinized polybutadiene) may be incorporated into the polyurethane polymer through hydrolysis of an anhydride group and subsequent epoxy esterification with a group present on the polyurethane polymer or a reactant used to form the polyurethane polymer.
4. A maleinized (poly)alkene compound (e.g., maleinized polybutadiene) may be incorporated into the polyurethane polymer via amide formation through reaction of the acid groups/anhydride group with a primary amine group on the polyurethane polymer or a reactant used to form the polyurethane polymer.
5. An epoxy-functional (poly)alkene compound may be incorporated into the polymer through reaction of an epoxy group with a carboxylic acid group present on the polymer or a reactant used to form the polymer, or through quaternary ammonium salt formation.
6. A (poly)alkene compound having acrylic or methacrylic functionality may be incorporated into the polyurethane polymer or a reactant used to form the polyurethane polymer via free radical polymerization.
7. A carboxylic acid-functional (poly)alkene compound may be incorporated into the polyurethane polymer or a reactant used to form the polyurethane polymer via esterification with hydroxyls or epoxy esterification with oxirane groups.

As discussed previously herein, the unsaturated polyurethane polymer of the present invention may include unsaturated bicyclic groups. Such bicyclic groups may be introduced in the polyurethane polymer of the present invention using any suitable process. For example, a reactant having (i) one or more unsaturated bicyclic groups and (ii) one or more active hydrogen groups may be used in forming the polyurethane. Non-limiting examples of such reactants include nadic acid or anhydride, tetrahydrophthalic acid or anhydride, methyl-nadic acid or anhydride, and mixtures thereof. Alternatively, a Diels-Alder reaction may be used to modify an unsaturated polyurethane polymer (or an unsaturated reactant to be further reacted to form the polyurethane polymer) to include an unsaturated bicyclic group, more preferably an unsaturated, bridged bicyclic group (e.g., a norbornene group). Materials and methods for producing a bicyclic Diels-Alder reaction product are discussed in WO 2008/124682. Non-limiting examples of useful Diels-Alder reactants may include anthracene, cyclohexadiene, cyclopentadiene (including, e.g., 1-alkyl cyclopentadienes or 2-alkyl cyclopentadienes), dicyclopentadiene, furan, thiophene, alpha terpine rosin, and combinations thereof.

In some embodiments, the unsaturated polyurethane polymer of the present invention includes one or more optional ether linkages. It was a surprising and unexpected result that certain cured coating compositions of the present invention that included a suitable amount of unsaturated polyurethane polymer having a suitable number of ether linkages exhibited significantly enhanced coating properties (e.g., coating hardness as determined by pencil hardness testing) as compared to cured coating compositions of the present invention that included an unsaturated polyurethane polymer lacking such ether linkages. While not intending to be bound by any theory, it is believed that the presence of such ether linkages can contribute to the formation of crosslinks upon coating cure. Such crosslinks are believed to be formed between aliphatic carbon-carbon double bonds of the polyurethane polymer (as intra-polymer crosslinks within the same polymer strand or crosslinks between separate polymer strands).

In some embodiments, the unsaturated polyurethane polymer preferably includes an efficacious amount of ether linkages. A useful measure of the amount of ether linkages present in a polymer is the total mass of ether oxygen relative to the total mass of the polymer. As used herein the term "ether oxygen" refers to the oxygen atom present in an ether linkage. Thus, for example, the total mass of ether oxygen present in a polymer does not include the mass of any non-ether oxygen atoms that may be present, for example, in a polyether segment. In some embodiments, the unsaturated polyurethane polymer of the present invention includes at least about 1 wt-% of ether oxygen, more preferably at least 1.5 wt-% of ether oxygen, and even more preferably at least 3.0 wt-% of ether oxygen. The upper range of ether linkages present in the unsaturated polyurethane polymer is not particularly limited, but the polymer will typically include less that about 6 wt-% or less than about 4.5 wt-% of ether oxygen.

Any suitable compound may be used to incorporate the optional ether linkages into the unsaturated polyurethane polymer. Functionalized ether or polyether compounds can be used such as, for example, an ether-containing ethylene glycol (e.g., diethylene glycol, triethylene glycol, tetraethylene glycol, etc.); an ether-containing propylene glycol (e.g., dipropylene glycol, tripropylene glycol, tetrapropylene glycol, etc.); an ether-containing butylene glycol (e.g., dibutylene glycol, tributylene glycol, tetrabutylene glycol, etc.); a polyethylene glycol; a polypropylene glycol; polybutylene glycol; or a copolymer or mixture thereof. In some embodiments, a functionalized ether- or polyether-containing compound is attached to one or more other portions of the polyurethane polymer via one or more step-growth linkages (e.g., ester linkages). In certain embodiments, a structural unit derived from an ether- or polyether-containing compound is located in a backbone of the unsaturated polyurethane polymer and is attached on at least one end, and in some instances both ends, to another portion of the polyurethane backbone via a step-growth linkage (e.g., an ester linkage).

It is contemplated that the benefits of ether linkages may also be realized, at least in part, by incorporating an efficacious amount of ether linkages into one or more other components of the coating composition. For example, the coating composition may include a second polymer that includes a suitable amount of ether linkages such as, for example, an amount pursuant to that described above for the unsaturated polyurethane polymer. The ether linkages may also be present in a non-polymer ingredient such as, for example, a volatile organic compound such as tripropylene glycol or the like.

In preferred embodiments, the coating composition of the present invention preferably includes one or more optional liquid carriers. Preferably, the liquid carrier(s) are selected to provide a dispersion or solution of the unsaturated polyurethane polymer of the present invention for further formulation. The liquid carrier can be an organic solvent or mixture of organic solvents, water, or a combination thereof. Depending upon the particular embodiment, the coating composition can be a water-based coating composition or a solvent-based coating composition. Non-limiting examples of suitable organic solvents for use in the water-based and/or solvent-based coating compositions of the present invention include aliphatic hydrocarbons (e.g., mineral spirits, kerosene, VM&P NAPHTHA solvent, and the like); aromatic hydrocarbons (e.g., benzene, toluene, xylene, the SOLVENT NAPHTHA 100, 150, 200 products and the like); alcohols (e.g., ethanol, n-propanol, isopropanol, n-butanol, iso-butanol and the like); ketones (e.g., acetone, 2-butanone, cyclohexanone, methyl aryl ketones, ethyl aryl ketones, methyl isoamyl ketones, and the like); esters (e.g., ethyl acetate, butyl acetate and the like); glycols (e.g., butyl glycol); glycol ethers (e.g., ethylene glycol monomethyl ether, ethylene glycol monoethyl ether, ethylene glycol monobutyl ether, propylene glycol monomethyl ether, and the like); glycol ether esters (e.g., butyl glycol acetate, methoxypropyl acetate and the like); and mixtures thereof.

The coating composition of the present invention typically has a total solids content of from about 10 to about 75 wt-%. In some embodiments, such as, for example, certain water-based embodiments, the coating composition preferably has a total solids of at least about 20 wt-% and more preferably at least about 30 wt-%. The coating composition preferably has a total solids of less than about 50 wt-%, and more preferably less than about 40 wt-%.

In some embodiments, the coating composition is a solvent-based coating composition that preferably includes no more than a de minimus amount (e.g., 0 to 2 wt-%) of water. In other embodiments, the coating composition can include a substantial amount of water.

In some embodiments, the coating composition is prepared using one or more hydroxyl-functional organic solvents. Non-limiting examples of suitable hydroxyl-functional organic solvents include any of the alcohols described above, methanol, 2-butanol, t-butanol, n-pentanol and isomers of pentanol, n-hexanol and isomers of hexanol, diacetone alcohol, benzyl alcohol, ethylene glycol, propylene glycol, 1,3-propane diol, 1,3-butane diol, 1,4-butane diol, ethylene glycol monomethyl ether, ethylene glycol monoethyl ether, ethylene glycol monopropyl ether, ethylene glycol mono n-butyl ether, ethylene glycol mono-n-hexyl ether, propylene glycol monomethyl ether, propylene glycol monoethyl ether, propylene glycol monopropyl ether, propylene glycol mono-n-butyl ether, propylene glycol mono-t-butyl ether, propylene glycol mono phenyl ether, diethyleneglycol mono-methyl ether, diethylene glycol mono-ethyl ether, diethylene glycol mono-propyl ether, diethylene glycol mono butyl ether, dipropylene glycol monomethyl ether, dipropylene glycol monomethyl ether, dipropylene monoethyl ether, dipropylene glycol monopropyl ether, dipropylene glycol monobutyl ether, tripropylene glycol monomethyl ether, tripropylene glycol monoethyl ether, tripropylene glycol monobutyl ether, 2,2,4-trimethyl-1,3-pentandiol monoisobutyl ester, and combinations thereof. If used, the one or more hydroxyl-functional organic solvents are typically present in the coating composition in an amount of from about 1% to about 50%, more preferably from about 5% to about 40%, and even more preferably about 10% to about 30%.

In some embodiments, the coating composition preferably includes at least about 10 wt-%, more preferably at least about 20 wt-%, and even more preferably at least about 30 wt-% of water, based on the total weight of the coating composition. In some such embodiments, the coating composition preferably includes less than about 60 wt-%, more preferably less than about 50 wt-%, and even more preferably less than about 40 wt-% of water, based on the total weight of the coating composition. In some water-containing embodiments, the coating composition preferably includes one or more organic solvents in an amount from about 10 to about 70 wt-%, more preferably from about 20 to about 60 wt-%, and even more preferably from about 25 to about 45 wt-%, based on the total weight of the coating composition. The inclusion of a suitable amount of organic solvent in certain water-based coating compositions of the present invention may be advantageous, for example, for certain coil coating applications to modify flow and leveling of the coating composition, control blistering, and maximize the line speed of the coil coater. Moreover, vapors generated from evaporation of the organic solvent during coating cure may be used to fuel the curing ovens. The ratio of water to organic solvent in the coating composition can vary widely depending on the particular coating end use and application methodology.

In some embodiments, the weight ratio of water to organic solvent in the final coating composition ranges from about 0.1:1 to 10:1 (water:organic solvent), more preferably from about 0.2:1 to 5:1, and even more preferably from about 0.7:1 to 1.3:1.

When an aqueous dispersion is desired, the unsaturated polyurethane polymer of the present invention may be rendered water-dispersible using any suitable means, including the use of non-ionic water-dispersing groups, salt groups, surfactants, or a combination thereof. As used herein, the term "water-dispersing groups" also encompasses water-solubilizing groups. In certain preferred embodiments, the unsaturated polyurethane polymer contains a suitable amount of water-dispersing groups, preferably salt and/or salt-forming groups, such that the polymer is capable of forming a stable aqueous dispersion with an aqueous carrier.

In water-based coating embodiments, the unsaturated polyurethane polymer is typically dispersed using salt groups. A salt (which can be a full salt or partial salt) is typically formed by neutralizing or partially neutralizing salt-forming groups (e.g., acidic or basic groups) of the polyurethane polymer with a suitable neutralizing agent. Alternatively, the polyurethane polymer may be formed from ingredients including preformed salt groups. The degree of neutralization required to form the desired polymer salt may vary considerably depending upon the amount of salt-forming groups included in the polymer, and the degree of solubility or dispersibility of the salt which is desired. Ordinarily in making the polymer water-dispersible, the salt-forming groups (e.g., acid or base groups) of the polymer are at least 25% neutralized, preferably at least 30% neutralized, and more preferably at least 35% neutralized, with a neutralizing agent in water. Non-limiting examples of suitable salt groups include anionic salt groups, cationic salt groups, or combinations thereof.

Non-limiting examples of anionic salt groups include neutralized acid or anhydride groups, sulphate groups (—OSO$_3^-$), phosphate groups (—OPO$_3^-$), sulfonate groups (—SO$_2$O$^-$), phosphinate groups (—POO$^-$), phosphonate groups (—PO$_3^-$), and combinations thereof. Non-limiting examples of suitable cationic salt groups include:

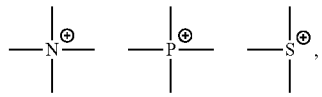

(referred to, respectively, as quaternary ammonium groups, quaternary phosphonium groups, and tertiary sulfate groups) and combinations thereof. Non-limiting examples of non-ionic water-dispersing groups include hydrophilic groups such as ethylene oxide groups. Compounds for introducing the aforementioned groups into polymers are known in the art.

Non-limiting examples of neutralizing agents for forming anionic salt groups include inorganic and organic bases such as an amine, sodium hydroxide, potassium hydroxide, lithium hydroxide, ammonia, and mixtures thereof. In certain embodiments, tertiary amines are preferred neutralizing agents. Non-limiting examples of neutralizing agents for forming cationic salt groups include organic and inorganic acids such as formic acid, acetic acid, hydrochloric acid, lactic acid, sulfuric acid, and combinations thereof.

When acid or anhydride groups are used to impart water dispersibility, the acid- or anhydride-functional polyurethane polymer preferably has an acid number of at least 5, and more preferably at least 40 milligrams (mg) KOH per gram resin. The acid-functional polyurethane polymer preferably has an acid number of no greater than 400, and more preferably no greater than 100 mg KOH per gram resin.

Alternatively, a surfactant may be used in place of water-dispersing groups to aid in dispersing the polyurethane in an aqueous carrier. Non-limiting examples of suitable surfactants include alkyl sulfates (e.g., sodium lauryl sulfate), ether sulfates, phosphate esters, sulphonates, and their various alkali, ammonium, amine salts and aliphatic alcohol ethoxylates, alkyl phenol ethoxylates, and mixtures thereof.

The coating composition of the present invention may optionally include one or more vinyl polymers. For example, vinyl polymers such as those described in U.S. Application No. 61/243,888 can be included. The unsaturated polyurethane polymer of the present invention and the vinyl polymer can be present as separate polymers (i.e., polymers that are not covalently attached to one another), covalently attached polymers, or a mixture thereof. Optional covalent linkages may be formed between the polyurethane and the vinyl polymer at any suitable time, including prior to coating cure (e.g., during formation of the vinyl polymer), during and/or after coating cure, or a combination thereof. In some embodiments, the unsaturated polyurethane polymer and the vinyl polymer are not covalently attached while present in one or both of: a liquid coating composition or a cured coating resulting therefrom.

The optional vinyl polymer may be an acrylic polymer or a non-acrylic vinyl polymer. Typically, the vinyl polymer is formed via vinyl addition polymerization of an ethylenically unsaturated component. In some embodiments, the ethylenically unsaturated component is a mixture of monomers and/or oligomers that are capable of free radical initiated polymerization in aqueous medium. It is further contemplated that a cationic or anionic polymerization process may be used to form the vinyl polymer.

Suitable ethylenically unsaturated monomers and/or oligomers for inclusion in the ethylenically unsaturated component include, for example, alkyl (meth)acrylates; vinyl monomers; alkyl esters of maleic acid, fumaric acid, sorbic acid, or cinnamic acid; oligomers thereof; and mixtures thereof.

In certain embodiments, the vinyl polymer is an acrylic-containing vinyl polymer. Suitable alkyl (meth)acrylates include, for example, those having the structure: $CH_2=C(R^8)—CO—OR^9$ wherein $R^8$ is hydrogen or methyl, and $R^9$ is an alkyl group preferably containing one to sixteen carbon atoms. The $R^9$ group can be substituted with one or more, and typically one to three, moieties such as hydroxy, halo, phenyl, and alkoxy, for example. Suitable alkyl (meth) acrylates therefore encompass hydroxy alkyl (meth)acrylates. The alkyl (meth)acrylate typically is an ester of acrylic or methacrylic acid. Preferably, $R^8$ is hydrogen or methyl and $R^9$ is an alkyl group having two to twenty-two carbon atoms. More typically, $R^8$ is hydrogen or methyl and $R^9$ is an alkyl group having two to four carbon atoms.

Suitable alkyl (meth)acrylates include, but are not limited to, methyl (meth)acrylate, ethyl (meth)acrylate, propyl (meth)acrylate, isopropyl (meth)acrylate, butyl (meth)acrylate, isobutyl (meth)acrylate, pentyl (meth)acrylate, isoamyl (meth)acrylate, hexyl (meth)acrylate, 2-ethylhexyl (meth) acrylate, cyclohexyl (meth)acrylate, decyl (meth)acrylate, isodecyl (meth)acrylate, benzyl (meth)acrylate, lauryl (meth)acrylate, isobornyl (meth)acrylate, octyl (meth)acrylate, nonyl (meth)acrylate, hydroxyethyl acrylate (HEA), hydroxyethyl methacrylate (HEMA), hydroxypropyl (meth) acrylate (HPMA), glycidyl (meth)acrylate (GMA), and mixtures thereof.

Difunctional (meth)acrylate monomers may be used in the monomer mixture as well. Examples include ethylene glycol di(meth)acrylate, 1,6-hexanediol di(meth)acrylate, allyl (meth)acrylate, and the like.

Suitable vinyl monomers include, but are not limited to, styrene, methyl styrene, alpha-methylstyrene, halostyrene, isoprene, diallylphthalate, divinylbenzene, conjugated butadiene, vinyl toluene, vinyl naphthalene, and mixtures thereof.

Other suitable polymerizable vinyl monomers for use in the ethylenically unsaturated component include acrylonitrile, acrylamide, methacrylamide, methacrylonitrile, vinyl acetate, vinyl propionate, vinyl butyrate, vinyl stearate, N-isobutoxymethyl acrylamide, N-butoxymethyl acrylamide, acrylic acid, methacrylic acid, and mixtures thereof.

In some embodiments, at least 40 wt-% of the ethylenically unsaturated component used to form the vinyl polymer, more preferably at least 50 wt-%, will be selected from alkyl acrylates and methacrylates.

In some embodiments, the ethylenically unsaturated component includes one or more groups capable of forming a covalent linkage with one or more of the following: another group of the ethylenically unsaturated component, a group of the unsaturated polyurethane polymer, a group of another ingredient of the liquid composition (e.g., a crosslinking agent) and/or the finished coating composition. Some examples of such groups and covalent attachment methodologies are provided in International Application No. PCT/US10/42254.

The one or more optional vinyl polymers can be included in the coating composition in any suitable amount. In some embodiments, the coating composition includes at least 5 wt-%, more preferably at least 10 wt-%, even more preferably at least 25 wt-%, and even more preferably at least 50 wt-% of vinyl polymer, based on the total solids weight of vinyl polymer and unsaturated polyurethane polymer present in the coating composition. The coating composition preferably includes no greater than 95 wt-%, more preferably no greater than 90 wt-%, and even more preferably no greater than 85 wt-% of vinyl polymer, based on the total solids weight of vinyl polymer and unsaturated polyurethane polymer present in the coating composition.

In some embodiments, the vinyl polymer is formed in the presence of the unsaturated polyurethane polymer. In one such embodiment, the vinyl polymer is formed by polymerizing (e.g., emulsion polymerizing) an ethylenically unsaturated component in the presence of an aqueous dispersion including a water-dispersible unsaturated polyurethane polymer of the present invention. With regard to the conditions of the polymerization, the ethylenically unsaturated component is preferably polymerized in aqueous medium with a water-soluble free radical initiator in the presence of the water-dispersible polyurethane. For a further discussion of suitable polymerization techniques see U.S. application Ser. No. 12/505,236 filed on Jul. 17, 2009.

Certain preferred coating compositions of the present invention (e.g., compositions intended for food-contact applications) are substantially free of mobile bisphenol A (BPA) and aromatic glycidyl ether compounds (e.g., BADGE, BFDGE, and epoxy novalacs), more preferably essentially free of these compounds, even more preferably essentially completely free of these compounds, and most preferably completely free of these compounds. Certain preferred coating compositions (and, hence, the unsaturated polyurethane polymer) are also preferably substantially free of bound BPA and aromatic glycidyl ether compounds, more preferably essentially free of these compounds, most preferably essentially completely free of these compounds, and optimally completely free of these compounds.

Certain preferred unsaturated polyurethane polymers of the present invention are at least substantially "epoxy-free," more preferably "epoxy-free." The term "epoxy-free," when used herein in the context of a polymer, refers to a polymer that does not include any "epoxy backbone segments" (i.e., segments formed from reaction of an epoxy group and a group reactive with an epoxy group). Thus, for example, a polymer made from ingredients including an epoxy resin would not be considered epoxy-free. Similarly, a polymer having backbone segments that are the reaction product of a bisphenol (e.g., bisphenol A, bisphenol F, bisphenol S, 4,4'dihydroxy bisphenol, etc.) and a halohydrin (e.g., epichlorohydrin) would not be considered epoxy-free. However, a vinyl polymer formed from vinyl monomers and/or oligomers that include an epoxy moiety (e.g., glycidyl methacrylate) would be considered epoxy-free because the vinyl polymer would be free of epoxy backbone segments. In some embodiments, the coating composition of the present invention is also preferably at least substantially epoxy-free, more preferably epoxy-free.

In certain preferred embodiments, the unsaturated polyurethane polymer is "PVC-free," and preferably the coating composition is also "PVC-free." That is, each composition preferably contains less than 2 wt-% of vinyl chloride materials, more preferably less than 0.5 wt-% of vinyl chloride materials, and even more preferably less than 1 part per million (ppm) of vinyl chloride materials.

Coating compositions of the present invention may include an efficacious amount of one or more so called "metal driers." While not intending to be bound by any theory, it is believed that the presence of an efficacious amount of one or more metal driers may enhance crosslinking upon coating cure (e.g., by enhancing and/or inducing the formation of crosslinks between aliphatic carbon-carbon double bonds of the polyurethane polymer).

Non-limiting examples of suitable metal driers may include aluminum (Al), antimony (Sb), barium (Ba), bismuth (Bi), calcium (Ca), cerium (Ce), chromium (Cr), cobalt (Co), copper (Cu), iridium (Ir), iron (Fe), lead (Pb), lanthanum (La), lithium (Li), manganese (Mn), Neodymium (Nd), nickel (Ni), rhodium (Rh), ruthenium (Ru), palladium (Pd), potassium (K), osmium (Os), platinum (Pt), sodium (Na), strontium (Sr), tin (Sn), titanium (Ti), vanadium (V), Yttrium (Y), zinc (Zn), zirconium (Zr), any other suitable rare earth metal or transition metal, as well as oxides, salts (e.g., acid salts such as octoates, naphthenates, stearates, neodecanoates, etc.) or complexes of any of these, and mixtures thereof. The amount used will depend, at least partially, upon the particular drier(s) chosen for a particular end use. In general, however, the amount of metal drier present in the coating composition, if any, may suitably be greater than about 10 ppm by weight, preferably greater than about 25 ppm by weight, and more preferably greater than about 100 ppm by weight, based on the total weight of metal in the metal drier relative to the total weight of the coating composition. The amount of metal drier may suitably be less than about 10,000 ppm by weight, preferably less than about 1,000 ppm by weight, and more preferably less than about 600 ppm by weight, based on the total weight of metal in the metal drier relative to the total weight of the coating composition.

Coating compositions of the present invention may be formulated using one or more optional curing agents (i.e., crosslinking resins, sometimes referred to as "crosslinkers"). The choice of particular crosslinker typically depends on the particular product being formulated. Non-limiting examples of crosslinkers include aminoplasts, phenoplasts, blocked isocyanates, and combinations thereof.

The amount of crosslinker included, if any, may depend on a variety of factors, including, for example, the type of curing agent, the time and temperature of the bake, the molecular weight of the polymer, and the desired coating properties. If used, the crosslinker is typically present in an amount of up to 50 wt-%, preferably up to 30 wt-%, and more preferably up to 15 wt-%. If used, the crosslinker is typically present in an amount of at least 0.1 wt-%, more preferably at least 1 wt-%, and even more preferably at least 1.5 wt-%. These weight percentages are based upon the total weight of the resin solids in the coating composition.

Phenoplast resins include the condensation products of aldehydes with phenols. Formaldehyde and acetaldehyde are preferred aldehydes. Various phenols can be employed such as phenol, cresol, p-phenylphenol, p-tert-butylphenol, p-tert-amylphenol, and cyclopentylphenol.

Aminoplast resins include, for example, the condensation products of aldehydes such as formaldehyde, acetaldehyde, crotonaldehyde, and benzaldehyde with amino- or amido-group-containing substances such as urea, melamine, and benzoguanamine. Examples of suitable aminoplast resins include, without limitation, benzoguanamine-formaldehyde resins, melamine-formaldehyde resins, esterified melamine-formaldehyde, and urea-formaldehyde resins.

Condensation products of other amines and amides can also be employed such as, for example, aldehyde condensates of triazines, diazines, triazoles, guanadines, guanamines and alkyl- and aryl-substituted melamines. Some examples of such compounds are N,N'-dimethyl urea, benzourea, dicyandiimide, formaguanamine, acetoguanamine, glycoluril, ammelin 2-chloro-4,6-diamino-1,3,5-triazine, 6-methyl-2,4-diamino-1,3,5-triazine, 3,5-diaminotriazole, triaminopyrimidine, 2-mercapto-4,6-diaminopyrimidine, 3,4,6-tris(ethylamino)-1,3,5-triazine, and the like. While the aldehyde employed is typically formaldehyde, other similar condensation products can be made from other aldehydes, such as acetaldehyde, crotonaldehyde, acrolein, benzaldehyde, furfural, glyoxal and the like, and mixtures thereof.

Non-limiting examples of suitable isocyanate crosslinkers include blocked or non-blocked aliphatic, cycloaliphatic or aromatic di-, tri-, or poly-valent isocyanates, such as hexamethylene diisocyanate (HMDI), cyclohexyl-1,4-diisocyanate and the like, and mixtures thereof. Further non-limiting examples of generally suitable blocked isocyanates include isomers of isophorone diisocyanate, dicyclohexylmethane diisocyanate, toluene diisocyanate, diphenylmethane diisocyanate, phenylene diisocyanate, tetramethyl xylene diisocyanate, xylylene diisocyanate, and mixtures thereof. In some embodiments, blocked isocyanates are used that have an Mn of at least about 300, more preferably at least about 650, and even more preferably at least about 1,000.

For coating compositions of the present invention that employ a self-crosslinking embodiment of the unsaturated polyurethane polymer, it may not be necessary or desirable to include a separate curing agent such as a crosslinker.

The coating composition of the present invention may also include other optional polymers that do not adversely affect the coating composition or a cured coating resulting therefrom. Such optional polymers are typically included in a coating composition as a filler material, although they can be included as a crosslinking material, or to provide desirable properties. One or more optional polymers can be included in a sufficient amount to serve an intended purpose, but not in such an amount to adversely affect a coating composition or a cured coating composition resulting therefrom.

The coating composition of the present invention may also include other optional ingredients that do not adversely affect the coating composition or a cured coating composition resulting therefrom. Such optional ingredients include, for example, catalysts, dyes, pigments, toners, extenders, fillers, lubricants, anticorrosion agents, flow control agents, thixotropic agents, dispersing agents, antioxidants, adhesion promoters, light stabilizers, surfactants, and mixtures thereof. Each optional ingredient is preferably included in a sufficient amount to serve its intended purpose, but not in such an amount to adversely affect a coating composition or a cured coating composition resulting therefrom.

One preferred optional ingredient is a catalyst to increase the rate of cure. Examples of catalyst, include, but are not limited to, strong acids (e.g., dodecylbenzene sulphonic acid (DDBSA, available as CYCAT 600 from Cytec)), methane sulfonic acid (MSA), p-toluene sulfonic acid (pTSA), dinonylnaphthalene disulfonic acid (DNNDSA), and triflic acid), quaternary ammonium compounds, phosphorous compounds, tin and zinc compounds, and combinations thereof. Specific examples include, but are not limited to, a tetraalkyl ammonium halide, a tetraalkyl or tetraaryl phosphonium iodide or acetate, tin octoate, zinc octoate, triphenylphosphine, and similar catalysts known to persons skilled in the art. If used, a catalyst is preferably present in an amount of at least 0.01 wt-%, and more preferably at least 0.1 wt-%, based on the total weight of nonvolatile material in the coating composition. If used, a catalyst is preferably present in an amount of no greater than 3 wt-%, and more preferably no greater than 1 wt-%, based on the total weight of nonvolatile material in the coating composition.

Another useful optional ingredient is a lubricant (e.g., a wax), which facilitates manufacture of fabricated metal articles by imparting lubricity to sheets of coated metal substrate. Non-limiting examples of suitable lubricants include, for example, natural waxes such as Carnauba wax or lanolin wax, polytetrafluoroethane (PTFE) and polyethylene type lubricants. If used, a lubricant is preferably present in the coating composition in an amount of at least 0.1 wt-%, and preferably no greater than 2 wt-%, and more preferably no greater than 1 wt-%, based on the total weight of nonvolatile material in the coating composition.

Another useful optional ingredient is a pigment, such as titanium dioxide. If used, a pigment is preferably present in the coating composition in an amount of no greater than 70 wt-%, more preferably no greater than 50 wt-%, and even more preferably from 0.01 to 40 wt-%, based on the total weight of nonvolatile material in the coating composition.

Surfactants can be optionally added to the coating composition to aid in flow and wetting of the substrate. Examples of surfactants, include, but are not limited to, nonylphenol polyethers and similar surfactants known to persons skilled in the art. If used, a surfactant is preferably present in an amount of at least 0.01 wt-%, and more preferably at least 0.1 wt-%, based on the total weight of resin solids in the coating composition. If used, a surfactant is preferably present in an amount no greater than 10 wt-%, and more preferably no greater than 5 wt-%, based on the total weight of resin solids in the coating composition.

Preferred cured coatings of the present invention adhere well to metal (e.g., steel, tin-free steel (TFS), tin plate, electrolytic tin plate (ETP), aluminum, etc.) and provide high levels of resistance to corrosion or degradation that may be caused by prolonged exposure to corrosive environments (e.g., harsh weather conditions, intimate contact with food or beverage products, etc.).

The coating composition of the present invention has utility in a multitude of applications. The coating composition of the present invention may be applied, for example, as a mono-coat coating system direct to metal (or direct to pretreated metal), as a primer coat, as an intermediate coat, as a topcoat, or any combination thereof. The coating composition may be applied to planar metal stock such as is used, for example, for lighting fixtures; architectural metal skins (e.g., gutter stock, window blinds, siding and window frames); interior or exterior steel building products; HVAC applications; agricultural metal products; industrial coating applications (e.g., appliance coatings); packaging coating applications (e.g., food or beverage cans, drug cans, etc.) and the like. The coating composition is particularly suited for a coil coating operation where the composition is applied on planar metal coil substrate and then baked as the coated substrate travels toward an uptake coil winder.

The coating composition can be applied to a substrate using any suitable procedure including, for example, spray coating, roll coating, coil coating, curtain coating, immersion coating, meniscus coating, kiss coating, blade coating, knife coating, dip coating, slot coating, slide coating, vacuum coating, and the like, as well as other types of premetered coating. Other commercial coating applications and curing methods are also envisioned, including, for example, electrocoating, extrusion coating, laminating, powder coating, and the like.

The coating composition can be applied on a substrate prior to, or after, forming the substrate into an article. In some embodiments, at least a portion of a planar metal substrate (e.g., metal coil) is coated with a layer of the coating composition of the present invention, which is then cured before the planar substrate is formed (e.g., stamped) into an article.

After applying the coating composition onto a substrate, the composition can be cured using a variety of processes, including, for example, oven baking by either conventional or convectional methods, or any other method that provides an elevated temperature suitable for curing the coating. The curing process may be performed in either discrete or combined steps. For example, substrates can be dried at ambient temperature to leave the coating compositions in a largely un-crosslinked state. The coated substrates can then be heated to fully cure the compositions. In certain instances, coating compositions of the present invention can be dried and cured in one step.

The cure conditions will vary depending upon the method of application and the intended end use. The curing process may be performed at any suitable temperature, including, for example, oven temperatures in the range of from about 100° C. to about 300° C., and more typically from about 177° C. to about 250° C. If metal coil is the substrate to be coated, curing of the applied coating composition may be conducted, for example, by heating the coated metal substrate over a suitable time period to a peak metal temperature ("PMT") of preferably greater than about 350° F. (177° C.). More preferably, the coated metal coil is heated for a suitable time period (e.g., about 5 to 900 seconds) to a PMT of at least about 425° F. (218° C.).

In some embodiments, such as for example certain water-based coating applications, it may be possible to cure the coating composition of the present invention at a lower temperature, such as, for example, a PMT of greater than about 160° F., or from about 160° F. to 250° F. (i.e., from 71° C. to 121° C.). In such embodiments, it may be advantageous to include or more metal driers.

As previously discussed the coating composition of the present invention can be present as a layer of a mono-layer coating system or one or more layers of a multi-layer coating system. The coating thickness of a particular layer and the overall coating system will vary depending upon the coating material used, the coating application method, and the end use for the coated article. Mono-layer or multi-layer coil coating systems including one or more layers formed from a coating composition of the present invention may have any suitable overall coating thickness, but will typically have an overall average dry coating thickness of from about 5 to about 60 microns and more typically from about 10 to about 45 microns.

Preferred coatings of the present invention display one or more of the properties described in the Test Methods or Examples sections.

Some non-limiting embodiments of the present invention are provided below to further exemplify the present invention.

Embodiment 1

A method, comprising:
providing a coating composition comprising:
(i) an unsaturated polyurethane polymer having an iodine value of at least 10, and
(ii) a liquid carrier;
applying the coating composition to at least a portion of a planar metal substrate; and
heating the coated metal substrate to a peak metal temperature of at least 350° F. (177° C.) to form a crosslinked coating.

Embodiment 2

A composition, comprising:
a crosslinkable coating composition, comprising:
at least 30% by weight, based on total solids of the coating composition, of an unsaturated polyurethane polymer having an iodine value of at least 10;

a liquid carrier, wherein the liquid carrier preferably includes an amount of organic solvent that constitutes at least 15% by weight of the coating composition.

Embodiment 3

An article, comprising:
a metal substrate,
the coating composition of Embodiment 2 applied to at least a portion of the metal substrate.

Embodiment 4

The method, composition, or article of any of Embodiments 1-3, wherein the unsaturated polyurethane polymer is a self-crosslinkable polymer.

Embodiment 5

The method, composition, or article of any of Embodiments 1-4, wherein the unsaturated polyurethane polymer includes one or more aliphatic carbon-carbon double bonds.

Embodiment 6

The method, composition, or article of any of Embodiments 1-5, wherein the unsaturated polyurethane polymer includes one or more reactive aliphatic carbon-carbon double bonds.

Embodiment 7

The method, composition, or article of Embodiment 6, wherein the one or more reactive aliphatic carbon-carbon double bonds comprise a vinylic double bond, a conjugated double bond, a double bond present in a strained ring group, a double bond present in an unsaturated bicyclic group, or a combination thereof.

Embodiment 8

The method, composition, or article of any of Embodiments 1-7, wherein the unsaturated polyurethane polymer includes one or more unsaturated segments formed from an unsaturated polybutadiene compound, another (poly)alkene-containing compound, or a combination thereof.

Embodiment 9

The method, composition, or article of Embodiment 8, wherein the unsaturated polyurethane polymer is formed from reactants including, based on nonvolatile content, at least 1%, more preferably at least 5%, and even more preferably at least 15% by weight of a functionalized polybutadiene compound.

Embodiment 10

The method, composition, or article of any of Embodiments 1-9, wherein the unsaturated polyurethane polymer includes one or more ether linkages.

Embodiment 11

The method, composition, or article of any of Embodiments 1-10, wherein the unsaturated polyurethane polymer includes at least 1% by weight of ether oxygen.

Embodiment 12

The method, composition, or article of any of Embodiments 1-11, wherein the coating composition includes at least 30% by weight of the unsaturated polyurethane polymer, based on the total solids of the coating composition.

Embodiment 13

The method, composition, or article of any of Embodiments 1-12, wherein the coating composition further comprises one or more metal driers.

Embodiment 14

The method, composition, or article of Embodiment 13, wherein the coating composition comprises at least 100 ppm of the one or more metal driers.

Embodiment 15

The method, composition, or article of any of Embodiments 1-14, wherein the coating composition comprises an aqueous dispersion of the polyurethane polymer.

Embodiment 16

The method, composition, or article of any of Embodiments 1-14, wherein the coating composition comprises a solvent-based coating composition that may optionally include water.

Embodiment 17

The method, composition, or article of any of Embodiments 1-16, wherein the coating composition includes a liquid carrier that includes an amount of one or more organic solvents that constitutes at least 15% by weight of the coating composition.

Embodiment 18

The method, composition, or article of any of Embodiments 1-17, wherein the coating composition includes a liquid carrier that includes an amount of water that constitutes at least 10% by weight of the coating composition.

Embodiment 19

The method, composition, or article of any of Embodiments 1-14, wherein the coating composition comprises:
from 15 to 75% by weight of solids;
from 15 to 70% by weight of one or more organic solvents; and
from 10 to 70% by weight of water.

Embodiment 20

The method, composition, or article of any of Embodiment 1-14, wherein the coating composition comprises:
from 25 to 50% by weight of solids;
from 25 to 50% by weight of one or more organic solvents; and
from 25 to 50% by weight of water.

Embodiment 21

The method, composition, or article of any of Embodiments 1-20, wherein the coating composition further comprises a vinyl polymer.

Embodiment 22

The method, composition, or article of Embodiment 21, wherein the coating composition includes at least 5 wt-%, at least 10 wt-%, at least 25 wt-%, or at least 60 wt-% of vinyl polymer, based on the total solids weight of vinyl polymer and unsaturated polyurethane polymer included in the coating composition.

Embodiment 23

The method of any one of Embodiments 1-22, wherein the coated metal substrate is heated for 5 to 900 seconds to a PMT of at least 425° F. (218° C.) to form a crosslinked coating composition.

Embodiment 24

The method of any of Embodiments 1-23, further comprising forming the coated planar metal substrate, having the crosslinked coating disposed thereon, into an article.

Embodiment 25

The method, composition, or article of any of Embodiments 1-24, wherein the liquid carrier includes one or more hydroxyl-functional organic solvents in an amount that comprises at least 5% by weight of the coating composition.

Embodiment 26

The method, composition, or article of any of Embodiments 1-25, wherein the coating composition, when applied to a planar chrome metal coil substrate at an average dry film weight of 9.3 grams per square meter and cured for 10 seconds in a heated oven to achieve a PMT of 253° C. to yield a cured coating, initially passes less than 10 milliamps (mA), more preferably less than 5 mA, most preferably less than 2 mA, and optimally less than 1 mA when subjected to the Fabrication Test described below.

Test Methods

Unless indicated otherwise, the following test methods were utilized in the Examples that follow.

A. Solvent Resistance

The extent of "cure" or crosslinking of a coating is measured as a resistance to solvents, such as methyl ethyl ketone (MEK, available from Exxon, Newark, N.J.). This test is performed as described in ASTM D 5402-93. The number of double-rubs (i.e., one back-and forth motion) is reported. This test is often referred to as "MEK Resistance."

B. Adhesion

Adhesion testing is performed to assess whether the coating adheres to the coated substrate. The adhesion test was performed according to ASTM D 3359—Test Method B, using SCOTCH 610 tape (available from 3M Company of Saint Paul, Minn.). Adhesion is generally rated on a scale of 0-10 where a rating of "10" indicates no adhesion failure, a rating of "9" indicates 90% of the coating remains adhered, a rating of "8" indicates 80% of the coating remains adhered, and so on.

C. Blush Resistance

Blush resistance measures the ability of a coating to resist attack by various solutions. Typically, blush is measured by the amount of water absorbed into a coated film. When the film absorbs water, it generally becomes cloudy or looks white. Blush is generally measured visually using a scale of 0-10 where a rating of "10" indicates no blush and a rating of "0" indicates complete whitening of the film. Blush ratings of at least 7 are typically desired for commercially viable coatings and optimally 9 or above.

D. Acidified Coffee Testing

An acidified coffee solution was prepared by dissolving 4 grams of citric acid per liter of brewed coffee. Coated substrate samples (2 inch by 4 inch coated metal strip reverse impacted, after coating, in the center of the strip) were placed in a vessel and partially immersed in the acidified coffee solution. While partially immersed, the coated substrate samples were placed in an autoclave and subjected to heat of 121° C. and pressure of 1 atm above atmospheric pressure for a time period of 60 minutes. After the time was complete, the samples were immersed in cool tap water, rinsed with tap water, and then stored in water (deionized or tap) until tested for adhesion, blush resistance, or stain resistance. Adhesion and blush resistance was performed using the methods described herein. Stain resistance was assessed visually on a scale of 0 to 10, with a "0" indicating that the coating was stained as dark as the coffee grinds, a "5" indicating moderate staining of the coating (e.g., as indicated by the test piece being quite gold in color), and a "10" indicating no detectable staining of the coating.

E. Dowfax Detergent Test

The "Dowfax" test is designed to measure the resistance of a coating to a boiling detergent solution. The solution is prepared by mixing 5 ml of DOWFAX 2A1 (product of Dow Chemical) into 3000 ml of deionized water. Typically, coated substrate strips are immersed into the boiling Dowfax solution for 15 minutes. The strips are then rinsed and cooled in deionized water, dried, and then tested and rated for blush and adhesion as described previously.

F. Pencil Hardness

This test measures the hardness of a cured coating. Pencil hardness was assessed using ASTM D3363, with the test run against metal grain. The data is reported in the form of the last successful pencil prior to film rupture. Thus, for example, if a coating does not rupture when tested with a 2H pencil, but ruptures when tested with a 3H pencil, the coating is reported to have a pencil hardness of 2H.

G. Fabrication Test

This test measures the ability of a coated substrate to retain its integrity as it undergoes the formation process necessary to produce a fabricated article such as a beverage can end. It is a measure of the presence or absence of cracks or fractures in the formed end. The end is typically placed on a cup filled with an electrolyte solution. The cup is inverted to expose the surface of the end to the electrolyte solution. The amount of electrical current that passes through the end is then measured. If the coating remains intact (no cracks or fractures) after fabrication, minimal current will pass through the end.

For the present evaluation, fully converted 202 standard opening beverage ends were exposed for a period of 4 seconds to a room-temperature electrolyte solution comprised of 1% NaCl by weight in deionized water. The coating to be evaluated was present on the interior surface of the beverage end at a dry film thickness of 6 to 7.5 milligrams per square inch ("msi") (or 9.3 to 11.6 grams per square meter), with 7 msi being the target thickness. Metal exposure was measured using a WACO Enamel Rater II (available from the Wilkens-Anderson Company, Chicago, Ill.) with an output voltage of 6.3 volts. The measured electrical current, in milliamps, is reported. End continuities are typically tested initially and then after the ends are subjected to pasteurization, dowfax, or retort.

Preferred coatings of the present invention initially pass less than 10 milliamps (mA) when tested as described above, more preferably less than 5 mA, most preferably less than 2 mA, and optimally less than 1 mA. After pasteurization, dowfax, or retort, preferred coatings give continuities of less than 20 mA, more preferably less than 10 mA, even more preferably less than 5 mA, and even more preferably less than 2 mA.

H. Iodine Value

Iodine values were determined using ASTM D 5758-02 (Reapproved 2006) entitled "Standard Method for Determination of Iodine Values of Tall Oil Fatty Acids," and are expressed in terms of centigrams of iodine per gram of resin. Methylene chloride (HPLC grade or better) was used as the diluent solvent in place of iso-octane or cyclohexane.

EXAMPLES

The present invention is illustrated by the following examples. It is to be understood that the particular examples, materials, amounts, and procedures are to be interpreted broadly in accordance with the scope and spirit of the present inventions as set forth herein. Unless otherwise indicated, all parts and percentages are by weight. Unless otherwise specified, all chemicals used are commercially available from, for example, Sigma-Aldrich, St. Louis, Mo.

Example 1

Polyurethane Polymer

TABLE 1

| INGREDIENT | Amount (grams) |
|---|---|
| 1. Tripropylene glycol/isophthalic acid polyester | 80.30 g |
| 2. Poly BD R45HTLO[A] | 40.15 g |
| 3. Propylene glycol/dimer fatty acid polyester | 40.15 g |
| 4. Dimethylolpropionic acid | 12.63 g |
| 5. Isophorone diisocyanate | 51.33 g |
| 6. Dipropylene glycol dimethyl ether | 85.70 g |
| 7. Methyl methacrylate | 147.14 g |
| 8. 2,6-di-tertbutyl-4-methyl phenol | 0.07 g |
| 9. Triethylamine | 4.76 g |
| 10. Deionized water | 462.45 g |
| 11. Propylene glycol monomethyl ether | 88.40 g |
| 12. Deionized water | 32.74 g |
| 13. Aminoethylethanol amine | 6.48 g |
| 14. Methyl methacrylate | 67.31 g |
| 15. n-butyl acrylate | 89.18 g |
| 16. Glycidyl methacrylate | 43.37 g |
| 17. Propylene glycol monomethyl ether | 50.41 g |
| 18. Tert-butyl hydro peroxide (70% aq) | 0.99 g |
| 19. Deionized water | 63.01 g |
| 20. Isoascorbic acid | 0.99 g |
| 21. Sodium feredetate (7% aq) | 0.04 g |
| 22. Triethylamine | 0.50 g |
| 23. Deionized water | 49.11 g |

[A]The Poly BD R45HTLO product is commercially available from Sartomer Company, Inc., Exton, PA.

Items 1 through 8 of Table 1 were charged to a two-liter round bottom flask equipped with a stirrer, an air sparge, a thermocouple, and a heating mantle. These items were mixed until uniform, and then the contents of the flask were heated gradually to 88° C. over about 1 hour. After the reactor reached 88° C., it was held at this temperature for 3 hours and the isocyanate content was titrated to ensure that the isocyanate hydroxyl reaction was complete. The batch was then cooled to 54° C. over about 1 hour and item 9 was added to the reactor and the contents were allowed to mix for about 3 minutes. In a separate three-liter stainless steel pot equipped with a thermocouple, a nitrogen blanket, and agitation, items 10 and 11 were added. These materials were chilled to 10 to 12° C. prior to addition to the pot. The contents of the two-liter flask (urethane prepolymer) were then dispersed into the water and solvent in the three-liter pot over 3 to 5 minutes. (It is normal to lose approximately 5% of the prepolymer due to the material clinging to the walls of the two-liter flask. The amounts of the other materials in the formulation are prorated appropriately to keep the ratios of materials the same as listed above.)

After all of the prepolymer was in the dispersion pot, items 12 and 13 were added as a premix. The batch was then allowed to exotherm and was stirred for approximately 35 to 45 minutes to allow the amine/isocyanate chain extension reaction to proceed.

Example 2

Polyurethane/Acrylic Dispersion

After the 35 to 45 minute hold of Example 1, items 14, 15, and 16 were added as a premix and item 17 was added as a rinse for the premix container. After about 10 minutes of mixing time, item 18 was added to the dispersion pot and a premix of items 19 to 22 was added to the batch at an even rate over about 20 to 30 minutes. During this addition, the batch was allowed to exotherm. After the exotherm peaked and the temperature began to fall, item 23 was added slowly to adjust the solids of the material to approximately 41%. The measured iodine value of the finished dispersion was about 16 (accordingly, the polyurethane had a calculated iodine value of about 95) and the viscosity was 120 cps.

Example 3

Coating Composition

A coating composition was formed using the ingredients of Table 2 below.

TABLE 2

| INGREDIENT | AMOUNT (in grams) |
|---|---|
| 1. Polyurethane/Acrylic Dispersion of Example 1 | 73.87 g |
| 2. Phenolic crosslinker | 1.60 g |
| 3. 2-butanol | 1.75 g |
| 4. Michelman 160PF[B] | 1.60 g |
| 5. Ethylene glycol | 12.93 g |

[B]The Michelman 160PF product is a lubricant wax commercially available from Michelman, Inc. of Cincinnati, Ohio.

Item 1 was charged to a stainless mixing vessel and agitated. Each of items 2-5 were added separately with good agitation. The resultant finish had a solids content of approximately 35% and a #4 Ford cup viscosity of 16 seconds.

Example 4

Coated Article

The coating composition of Example 3 was applied as a coil coating to chrome-pretreated aluminum metal coil. Steps were taken to improve flow and leveling prior to a 10-second dwell in an oven to achieve a 253° C. peak metal temperature (PMT) and cure the coating.

The cured coating samples were tested for a variety of coating properties. The data for some of the coating property tests are included in Table 3 below.

TABLE 3

| Coating Composition | Example 3 |
|---|---|
| Film Weight (mg/in2) | 6 to 7 mg/in2 |
| Pencil Hardness | F |
| MEK Resistance | >100 MEK Double Rubs |
| Coffee Process | |
| Stain | 4 |
| Blush | 10 |
| Adhesion | 7 |
| Fabrication | |
| Initial (prior to Dowfax)* | 0.2 mA |
| After Dowfax* | 0.4 mA |

*202 Beverage Can Ends coated on interior surface.

The complete disclosure of all patents, patent applications, and publications, and electronically available material cited herein are incorporated by reference. The foregoing detailed description and examples have been given for clarity of understanding only. No unnecessary limitations are to be understood therefrom. The present invention is not limited to the exact details shown and described, for variations obvious to one skilled in the art will be included within the present invention defined by the claims.

What is claimed is:

1. A method of coil coating comprising:
    providing a coating composition comprising:
        about 30% by weight of an unsaturated polyurethane polymer having an iodine value of at least 10 and no more than 200 and including about 1% to about 6% by weight of ether oxygen, based on the total solids of the coating composition; and
        a liquid carrier including an amount of one or more organic solvents that constitutes at least 15% by weight of the coating composition;
    applying the coating composition to at least a portion of a planar metal substrate; and
    heating the coated metal substrate to a peak metal temperature of at least 177° C. to form a crosslinked coating.

2. The method of claim 1, wherein the unsaturated polyurethane polymer is a self-crosslinkable polymer.

3. The method of claim 1, wherein the polyurethane polymer includes one or more aliphatic carbon-carbon double bonds that comprise a vinylic double bond, a conjugated double bond, a double bond present in a strained ring group, a double bond present in an unsaturated bicyclic group, or a combination thereof.

4. The method of claim 1, wherein the unsaturated polyurethane polymer includes one or more segments formed from an unsaturated polybutadiene compound.

5. The method of claim 4, wherein the unsaturated polyurethane polymer is formed from ingredients including, based on nonvolatile content, at least 5% by weight of the polybutadiene compound.

6. The method of claim 1, wherein the unsaturated polyurethane polymer includes about 3.0 to 4.5% by weight of ether oxygen.

7. The method of claim 1, wherein the unsaturated polyurethane polymer includes one or more structural units derived from diethylene glycol, triethylene glycol, tetraethylene glycol, dipropylene glycol, tripropylene glycol, tetrapropylene glycol, dibutylene glycol, tributylene glycol, tetrabutylene glycol, a polyethylene glycol, a polypropylene glycol, a polybutylene glycol, or a combination thereof.

8. The method of claim 1, wherein the coating composition further comprises one or more metal driers.

9. The method of claim 1, wherein the coating composition comprises an aqueous dispersion of the polyurethane polymer.

10. The method of claim 1, wherein the liquid carrier includes an amount of water that constitutes at least 10% by weight of the coating composition.

11. The method of claim 1, wherein the coating composition comprises:
    from 25 to 50% by weight of solids;
    from 25 to 50% by weight of one or more organic solvents; and
    from 25 to 50% by weight of water.

12. The method of claim 1, wherein the coating composition further comprises a vinyl polymer.

13. The method of claim 1, wherein the coated metal substrate is heated for 5 to 900 seconds to a peak metal temperature of at least 218° C. to form the crosslinked coating composition.

14. The method of claim 1, further comprising forming the coated planar metal substrate, having the crosslinked coating disposed thereon, into an article.

15. An article prepared according to the method of claim 1.

* * * * *